United States Patent
Haviv et al.

(10) Patent No.: US 6,753,408 B1
(45) Date of Patent: Jun. 22, 2004

(54) PEPTIDES HAVING ANTIANGIOGENIC ACTIVITY

(76) Inventors: Fortuna Haviv, 1125 Oxford Rd., Deerfield, IL (US) 60015; Jack Henkin, 1370 Lincoln Ave. South, Highland Park, IL (US) 60035; Michael F. Bradley, 3930 N. Pine Grove Ave., Apt. #2405, Chicago, IL (US) 60613; Douglas M. Kalvin, 1201 Lockwood Dr., Buffalo Grove, IL (US) 60089; Andrew J. Schneider, 980 Cheswick Dr., Gurnee, IL (US) 60031

( * ) Notice: Subject to any disclaimer, the term of this patent is extended or adjusted under 35 U.S.C. 154(b) by 44 days.

(21) Appl. No.: 09/718,591

(22) Filed: Nov. 22, 2000

Related U.S. Application Data

(60) Provisional application No. 60/166,791, filed on Nov. 22, 1999.

(51) Int. Cl.$^7$ .................................................. C07K 7/00
(52) U.S. Cl. ......................................... 530/328; 514/15
(58) Field of Search .............................. 530/328; 514/15

(56) References Cited

U.S. PATENT DOCUMENTS

| | | | |
|---|---|---|---|
| 5,190,918 A | 3/1993 | Deutch et al. | 514/15 |
| 5,192,744 A | 3/1993 | Bouck et al. | 514/8 |
| 5,200,397 A | 4/1993 | Deutch et al. | 514/15 |
| 5,426,100 A | 6/1995 | Deutch et al. | 514/15 |

FOREIGN PATENT DOCUMENTS

| | | |
|---|---|---|
| EP | 0 443 404 | 8/1991 |
| WO | 93 16716 | 9/1993 |
| WO | 97 41824 | 11/1997 |
| WO | 98 41542 | 9/1998 |

OTHER PUBLICATIONS

Donoviel, et al., *J. Biological Chemistry*, vol. 263 (35), 1988, pp. 18590–18593.

Folkman, *Cancer Research*, vol. 46, 1986, pp. 467–473.

Folkman, et al., *Science*, vol. 235, 1987, pp. 442–447.

Folkman, et al., *The Journal of Biological Chemistry*, vol. 264 (12), 1989, pp. 6892–6897.

Folkman, *Journal of the National Cancer Institute*, vol. 82 (1), 1990, pp. 4–6.

Gasparini, et al., *J. Clinical Oncology*, vol. 13 (3), 1995, pp. 765–782.

Haverstick, et al., *Biochemistry*, vol. 23, 1984, pp. 5597–5603.

Hennessy, et al., *J. Cell Biology*, vol. 108, 1989, pp. 729–736.

Lawler, et al., *J. Cell Biology*, vol. 103, 1986, pp. 1635–1648.

Majack, et al., *Cell Membranes Methods–Reviews*, vol. 3, 1987, pp. 55–77.

Prescott, Ed., *Methods in Cell Biology*, vol. XIV, Academic Press, New York, N.Y., 1976, pp. 33 et seq.

Santoro, et al., *Methods in Enzymology*, vol. 144, 1987, pp. 438–446.

Tolsma, et al., *J. Cell Biol.*, vol. 122 (2), 1993, pp. 497–511.

Weidner, et al., *The New England Journal of Medicine*, vol. 324 (1), 1991, pp. 1–8.

U.S. patent application Ser. No. 09/316,888, filed May 21, 1999.

U.S. patent applicatiion Ser. No. 60/166,791, filed Nov. 22, 1999.

*Primary Examiner*—Christopher S. F. Low
*Assistant Examiner*—David Lukton
(74) *Attorney, Agent, or Firm*—B. Gregory Donner; Johanna M. Corbin

(57) ABSTRACT

Peptides of formula (I)

$$\text{Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11} \text{ (I)},$$

are useful for inhibiting angiogenesis. Also disclosed are angiogenesis-inhibiting compositions and methods of inhibiting angiogenesis in a mammal.

29 Claims, No Drawings

PEPTIDES HAVING ANTIANGIOGENIC ACTIVITY

CROSS-REFERENCE TO RELATED APPLICATIONS

This application claims priority to the provisional U.S. patent application Ser. No. 60/166,791, filed Nov. 22, 1999.

TECHNICAL FIELD

The invention relates to novel compounds having activity useful for treating conditions which arise or are exacerbated by angiogenesis, pharmaceutical compositions comprising the compounds, methods of treatment using the compounds, and methods of inhibiting angiogenesis.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days (Folkman, J. and Shing, Y., *The Journal of Biological Chemistry*, 267(16): 10931–10934, and Folkman, J. and Klagsbrun, M., *Science*, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., *Cancer Research*, 46: 467–473 (1986), Folkman, J., *Journal of the National Cancer Institute*, 82: 4–6 (1989)). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as the liver, the lung, and the bones (Weidner, N., et. al., *The New England Journal of Medicine*, 324(1): 1–8 (1991)).

Several angiogenesis inhibitors are currently under development for use in treating angiogenic diseases (Gasparini, G. and Harris, A. L., *J Clin Oncol* 13(3): 765–782, (1995)). A number of disadvantages have been associated with many of these compounds. A potent angiogenesis inhibitor, for example suramin, can cause severe systemic toxicity in humans at doses required to reach antitumor activity. Other compounds, such as retinoids, interferons, and antiestrogens are safe for human use, but have only a weak antiangiogenic effect.

A novel class of compounds having particularly effective in vitro and in vivo angiogenesis inhibiting properties, as well as a promising toxicity profile, has been described in commonly-owned U.S. patent application Ser. No. 09/316,888, filed May 21, 1999. Copending provisional U.S. patent application Ser. No. 60/166,924, filed Nov. 22, 1999, describes N-alkylated peptides having enhanced stability against in vivo enzymatic cleavage, improved pharmokinetics, and increased water solubility. Although peptidic compounds inhibiting angiogenesis have been described, it would be desirable to prepare analogs having a favorable toxicity profile which also exhibit improved angiogenesis inhibiting properties.

SUMMARY OF THE INVENTION

The present invention relates to a novel class of peptidic compounds exhibiting antiangiogenic activity. Compounds of the present invention generally have unnatural amino acids in the 3-position of the peptide. The residues in position 3 are structurally novel and can be neutral or charged. The novel substitution of the amino acyl residues in the 3-position of the peptide affords compounds having enhanced properties of angiogenesis inhibition.

In one aspect, the present invention provides a compound of formula (I)

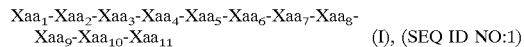

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$     (I), (SEQ ID NO:1)

or a pharmaceutically acceptable salt thereof, wherein $Xaa_1$ is absent or $Xaa_1$ is selected from the group consisting of hydrogen and an acyl group, wherein the acyl group is selected from the group consisting of
$R^1$—$(CH_2)_n$—$C(O)$—, wherein n is an integer from 0 to 8 and $R^1$ is selected from the group consisting of N-acetylamino, alkoxy, alkyl, aryl, carboxy, cycloalkenyl, cycloalkyl, heterocycle, hydroxy; and
$R^2$—$CH_2CH_2$—$O$—$(CH_2CH_2O)_p$—$CH_2(O)$—, wherein p is an integer from 1 to 8 and $R^2$ is selected from the group consisting of hydrogen, N-acetylamino, and alkyl;

$Xaa_2$ is an amino acyl residue selected from the group consisting of
alanyl,
β-alanyl,
asparaginyl,
citrullyl,
N-ethylglycyl,
glutaminyl,
glutamyl,
methionyl,
N-methylalanyl,
N-methylprolyl,
prolyl,
pyro-glutamyl,
sarcosyl,
seryl,
threonyl,
$H_3C$—$C(O)$—$HN(CH_2)_q$—$C(O)$—, wherein q is an integer from 1 to 8, and
$H_3C$—$C(O)$—$HN$—$CH_2CH_2$—$O$—$(CH_2CH_2O)_r$—$CH_2$—$C(O)$—, wherein r is an integer from 1 to 8;
with the proviso that $Xaa_1$ is absent when $Xaa_2$ is N-methylprolyl, $H_3C$—$C(O)$—$HN$—$(CH_2)_q$—$C(O)$—, or $H_3C$—$C(O)$—$HN$—$CH_2CH_2$—$O$—$(CH_2CH_2O)_r$—$CH_2$—$C(O)$—;

$Xaa_3$ is an amino acyl residue selected from the group consisting of alanyl,
asparaginyl,
aspartyl,
glutaminyl,
glutamyl,
glycyl,
leucyl,
methionyl,
phenylalanyl,
prolyl, and
seryl;
$Xaa_4$ is an amino acyl residue selected from the group consisting of
alloisoleucyl,
allylglycyl,
2-aminobutyryl,
(1R,4S)-1-aminocyclopent-2-ene-4-carbonyl,
aspartyl,
3-(5-bromothien-2-yl)alanyl,
3-(3-chlorophenyl)alanyl,
3-(4-chlorophenyl)alanyl,
3-(3-cyanophenyl)alanyl,
cysteinyl(S-ethyl),
cysteinyl(S-methyl),
2,4-diaminobutanoyl,
2,3-diaminopropionyl,
3-(3,4-dimethoxyphenyl)alanyl,
3-(3-fluorophenyl)alanyl,
3-(4-fluorophenyl)alanyl,
histidyl,
homophenylalanyl,
homoseryl,
lysyl(N-epsilon-acetyl),
methionyl(sulfone),
methionyl(sulfoxide),
3-(4-methylphenyl)alanyl,
3-(naphth-1-yl)alanyl,
3-(naphth-2-yl)alanyl,
ornithyl,
phenylglycyl,
prolyl,
3-(3-pyridyl)alanyl,
seryl(O-benzyl),
styrylalanyl,
1,2,3,4-tetrahydroisoquinoline-3-carbonyl,
3-(thiazolyl)alanyl,
3-(thien-2-yl)alany),
D-3-(thien-2-yl)alanyl,
tryptyl,
tyrosyl, and
D-valyl;
$Xaa_5$ is an amino acyl residue selected from the group consisting of
D-alanyl,
alloisoleucyl,
D-alloisoleucyl,
D-allothreonyl,
D-allylglycyl,
D-2-aminobutyryl,
D-3-(4-aminophenyl)alanyl,
D-asparaginyl,
D-aspartyl,
D-3-(4,4'-biphenyl)alanyl,
D-t-butylglycyl,
D-3-(4-chlorophenyl)alanyl,
D-citrullyl,
D-3-(3-cyanophenyl)alanyl,
D-cyclohexylalanyl,
D-cyclohexylglycyl,
D-cysteinyl,
D-cysteinyl(S-t-butyl),
dehydroleucyl,
D-3-(3,4-difluorophenyl)alanyl,
D-3-(3,4-dimethoxyphenyl)alanyl,
D-glutaminyl,
D-glutamyl,
glycyl,
D-histidyl,
D-homoisoleucyl,
D-homophenylalanyl,
D-homoseryl,
isoleucyl,
D-isoleucyl,
D-leucyl,
D-lysyl,
D-lysyl(N-epsilon-nicotinyl),
D-methionyl,
D-3-(4-methylphenyl)alanyl,
D-3-(naphth-1-yl)alanyl,
D-3-(naphth-2-yl)alanyl,
D-neopentylglycyl,
D-3-(4-nitrophenyl)alanyl,
D-norleucyl,
D-norvalyl,
D-ornithyl,
D-penicillaminyl,
D-penicillaminyl(S-acetamidomethyl),
D-penicillaminyl(S-benzyl),
D-penicillaminyl(S-methyl),
D-phenylalanyl,
prolyl,
D-prolyl,
D-3-(3-pyridyl)alanyl,
D-seryl,
D-seryl(O-benzyl),
D-3-(thien-2-yl)alanyl,
D-threonyl,
D-threonyl(O-benzyl),
D-3-(3-trifluoromethylphenyl)alanyl,
D-3-(3,4,5-trifluorophenyl)alanyl,
D-tryptyl,
D-tyrosyl(O-benzyl),
D-tyrosyl(O-ethyl),
D-tyrosyl, and
D-valyl;
$Xaa_6$ is an amino acyl residue selected from the group consisting of
alanyl,
allothreonyl,
D-allothreonyl,
allylglycyl,
asparaginyl,
cysteinyl,
glutaminyl,
glycyl,
histidyl,
homoseryl,
D-homoseryl,
3-(4-hydroxymethylphenyl)alanyl,
isoleucyl,
lysyl(N-epsilon-acetyl),
methionyl,
3-(naphth-1-yl)alanyl,
3-(naphth-2-yl)alanyl, norvalyl,
octylglycyl,
ornithyl,
penicillaminyl,
prolyl,
3-(3-pyridyl)alanyl,
seryl,
D-seryl,
threonyl,
D-threonyl,
tryptyl, and
tyrosyl;
$Xaa_7$ is an amino acyl residue selected from the group
consisting of
alanyl,
allylglycyl,
2-aminobutyryl,
arginyl,
asparaginyl,
aspartyl,
3-(4-carboxyamidophenyl)alanyl,
citrullyl,
cyclohexylalanyl,
cysteinyl,
glutaminyl,
D-glutaminyl,
glutamyl,
glycyl,
histidyl,
homoalanyl,
homoleucyl,
homoseryl,
D-homoseryl,
isoleucyl,
leucyl,
D-leucyl,
lysyl(N-epsilon-acetyl),
lysyl(N-epsilon-isopropyl),
methionyl(sulfone),
methionyl(sulfoxide),
methionyl,
3-(naphth-1-yl)alanyl,
D-3-(naphth-1-yl)alanyl,
3-(naphth-2-yl)alanyl,
D-3-(naphth-2-yl)alanyl,
norleucyl,
norvalyl,
D-norvalyl,
octylglycyl,
penicillaminyl,
phenylalanyl,
propargylglycyl,
3-(3-pyridyl)alanyl,
seryl,
D-seryl,
threonyl,
tryptyl,
tyrosyl, and
valyl;
$Xaa_8$ is an amino acyl residue selected from the group
consisting of
alanyl,
alloisoleucyl,
D-alloisoleucyl,
allylglycyl,
aspartyl,
t-butylglycyl,
citrullyl,
cyclohexylglycyl,
cysteinyl,
glutamyl,
glycyl,
homoseryl,
isoleucyl,
D-isoleucyl,
leucyl,
lysyl(N-epsilon-acetyl),
methionyl,
3-(naphth-1-yl)alanyl,
3-(naphth-2-yl)alanyl,
norvalyl,
penicillaminyl,
phenylalanyl,
prolyl,
seryl,
tryptyl,
tyrosyl, and
valyl;
$Xaa_9$ is an amino acyl residue selected from
[(4-amino(N-isopropyl)methyl)phenyl]alanyl,
3-(4-amino-N-isopropylphenyl)alanyl,
arginyl,
arginyl($N^G N^{G'}$diethyl),
citrullyl,
3-(cyclohexyl)alanyl(4-N-isopropyl),
glycyl[4-piperidinyl(N-amidino)],
(3-guanidino)alanyl,
3-(4-guanidinophenyl)alanyl,
histidyl,
homoarginyl,
lysyl,
lysyl(N-epsilon-isopropyl),
lysyl(N-epsilon-nicotinyl),
norarginyl,
ornithyl(N-delta-isopropyl),
ornithyl(N-delta-nicotinyl),
ornithyl[N-delta-(2-imidazolinyl)],
[4-piperidinyl(N-amidino)]alanyl, and
[3-pyrrolidinyl(2-N-amidino)]alanyl;
$Xaa_{10}$ is an amino acyl residue selected from the group
consisting of
D-alanyl,
2-aminobutyryl,
2-aminoisobutyryl,
t-butylglycyl,
homoprolyl,
hydroxyprolyl,
isoleucyl,
leucyl,
phenylalanyl,
prolyl,
D-prolyl,
seryl,
1,2,3,4-tetrahydroisoquinoline-3-carbonyl,
threonyl, and
valyl;
$Xaa_{11}$ is a hydroxy group or an amino acid amide selected
from the group consisting of
D-alanylamide,
D-alanylethylamide,
azaglycylamide,
glycylamide,
glycylethylamide,
sarcosylamide, serylamide,
D-serylamide,
a residue represented by the formula

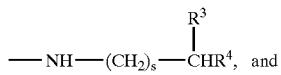

a group represented by the formula —NH—$R^5$;
wherein
s is an integer selected from 0 to 8;
$R^3$ is selected from the group consisting of hydrogen, alkyl, and a 5- to 6-membered cycloalkyl ring,
$R^4$ is selected from the group consisting of hydrogen, alkoxy, alkyl, aryl, cycloalkenyl, cycloalkyl, heterocycle, and hydroxy;
provided that s is not zero when $R^4$ is hydroxy or alkoxy; and
$R^5$ is selected from hydrogen, hydroxy, and cycloalkyl.

In another aspect, the present invention provides a composition for treating a patient in need of anti-angiogenesis therapy comprising a compound of formula (I) in combination with a pharmaceutically acceptable carrier.

Yet another aspect of the present invention provides a method for treating a patient in need of anti-angiogenesis therapy comprising administering to the patient a therapeutically effective amount of a compound of formula (I).

Still yet another aspect of the present invention provides a composition for the treatment of a disease selected from cancer, arthritis, psoriasis, angiogenesis of the eye associated with infection or surgical intervention, macular degeneration, and diabetic retinopathy comprising a compound of formula (I) in combination with a pharmaceutically acceptable carrier.

In yet another aspect, the present invention provides a method of isolating a receptor from an endothelial cell comprising binding a compound of formula (I) to the receptor to form a peptide receptor complex, isolating the peptide receptor complex, and purifying the receptor.

DETAILED DESCRIPTION OF THE INVENTION

Definition of Terms

As used herein, the singular forms "a", "an", and "the" include plural reference unless the context clearly dictates otherwise.

As used in the present specification the following terms have the meanings indicated:

The term "N-acetylamino," as used herein, refers to —NHC(O)CH$_3$.

The term "acyl," as used herein, refers to an alkyl group attached to the parent molecular moiety through a carbonyl group.

The term "alkoxy," as used herein, refers to an alkyl group attached to the parent molecular moiety through an oxygen atom.

The term "alkyl," as used herein, refers to a monovalent group derived from a straight or branched chain saturated hydrocarbon by the removal of a hydrogen atom. Preferred alkyl groups for the invention are $C_1$–$C_6$ alkyl groups having from one to six carbon atoms. Alkyl groups of one to three carbon atoms ($C_1$–$C_3$ alkyl) are more preferred for the invention.

The term "amino," as used herein, refers to —NH$_2$.

The term "aryl," as used herein, refers to a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like.

The term "carbonyl," as used herein, refers to —C(O)—.

The term "carboxy," as used herein, refers to —CO$_2$H.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include cyclohexenyl, octahydronaphthalenyl, norbornylenyl, and the like. The cycloalkenyl groups of the present invention can be optionally substituted with one, two, three, four, or five substituents independently selected from the group consisting of alkoxy, alkyl, carboxy, halo, and hydroxy.

The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo [3.1.1]heptyl, adamantyl, and the like. The cycloalkyl groups of the present invention can be optionally substituted with one, two, three, four, or five substituents independently selected from the group consisting of alkoxy, alkyl, carboxy, halo, and hydroxy.

The term "halo," as used herein, refers to F, Cl, Br, or I.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group. The heterocycle groups of the present invention can be attached through a carbon atom or a nitrogen atom in the group. Examples of heterocycles include, but are not limited to, furyl, thienyl, pyrrolyl, pyrrolidinyl, oxazolyl, thiazolyl, imidazolyl, imidazolinyl, pyrazolyl, isoxazolyl, isothiazolyl, piperidinyl, morpholinyl, thiomorpholinyl, piperazinyl, pyridinyl, indolyl, indolinyl, benzothienyl, and the like. The heterocycle groups of the present invention can be optionally substituted with one, two, three, or four substituents independently selected from the group consisting of alkoxy, alkyl, carboxy, halo, and hydroxy.

The term "hydroxy," as used herein, refers to —OH.

The term "nicotinyl," as used herein, refers to the acyl group derived from nicotinic acid, i.e. pyridine-3-carboxylic acid.

The term "nitrogen protecting group" or "N-protecting group," as used herein, refers to an easily removable group which is known in the art to protect an amino group against undesirable reaction during synthetic procedures and to be selectively removable. The use of nitrogen protecting groups is well known in the art for protecting groups against undesirable reactions during a synthetic procedure and many such protecting groups are known (see, for example, T. H. Greene and P. G. M. Wuts, Protective Groups in Organic Synthesis, 2nd edition, John Wiley & Sons, New York (1991). Examples of N-protecting groups include, are not limited to, acyl groups including acetyl, trifluoroacetyl, acylisothiocyanate, aminocaproyl, benzoyl and the like, and acyloxy groups, including t-butoxycarbonyl (Boc) and carbobenzyloxy (Cbz), 9-fluorenylmethoxycarbonyl (Fmoc), and the like.

The term "pharmaceutically acceptable ester," as used herein, refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "pharmaceutically acceptable solvate," as used herein, refers to an aggregate that comprises one or more molecules of the solute, such as a compound of formula (I), with one or more molecules of solvent.

The term "receptor," as used herein, refers to chemical groups or molecules on the cell surface or in the cell interior that have an affinity for a specific chemical group or molecule. Isolation of receptors relevant to the antiangiogenic activity of the peptide of the invention can provide useful diagnostic tools.

The term "shikimyl," as used herein, refers to the acyl residue derived from shikimic acid or [3R-(3α,4α,5β)-3,4,5-trihydroxy]-1-cyclohexene-1-carboxylic acid. A "dihydroshikimyl" group denotes the fully saturated analog of shikimic acid.

The term "succinyl," as used herein, refers to the acyl residue derived from succinic acid or (1,4-dioxobutyl)-1-carboxylic acid.

Unless indicated otherwise by a "D-" prefix, e.g. D-Ala or N-Me-D-Ile, the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides of this invention. The designation "R,S" is meant to indicate a racemic mixture of the two enantiomeric forms. This nomenclature follows that described in R. S. Cahn, et al., Angew. Chem. Int. Ed. Engl., 5, 385–415 (1966).

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide.

For the most part, the names on naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
| --- | --- |
| N—Ac—Sar | N-acetylsarcosyl |
| Ala | alanyl |
| β-Ala | β-alanyl |
| AlaNH$_2$ | alanylamide |
| AlaNH-ethyl | alanyl ethylamide |
| alloIle | alloisoleucyl |
| alloThr | allothreonyl |
| AllylGly | allylglycyl |
| 2-Abu | 2-aminobutyryl |
| (1R,4S)-AmCyeCO | (1R,4S)-1-aminocyclopent-2-ene-4-carbonyl |
| Aib | 2-aminoisobutyryl |
| AiPheAla | 3-(4-amino-N-isopropylphenyl)alanyl |
| AimPheAla | [(4-amino(N-isopropyl)methyl)phenyl]alanyl |
| 4-AmPheAla | 3-(4-aminophenyl)alanyl |
| Arg | arginyl |
| Arg(diethyl) | arginyl(N$^G$N$^{G'}$ diethyl) |
| Asn | asparaginyl |
| Asp | aspartyl |
| AzaGlyNH$_2$ | azaglycylamide |
| BiPheAla | 3-(4,4'-biphenyl)alanyl |
| 5-BrThiAla | 3-(5-bromothien2-yl)alanyl |
| Gly(t-Bu) | t-butylglycyl |
| CamdPheAla | 3-(4-carboxyamidophenyl)alanyl |
| 3-ClPheAla | 3-(3-chlorophenyl)alanyl |
| 4-ClPheAla | 3-(4-chlorophenyl)alanyl |
| Cit | citrullyl |
| 3-CNPheMa | 3-(3-cyanophenyl)alanyl |
| Cha | cyclohexylalanyl |
| Cha(Isp) | 3-(cyclohexyl)alanyl(N-isopropyl) |
| Chg | cyclohexylglycyl |
| Cys | cysteinyl |
| Cys(t-Bu) | cysteinyl(S-t-butyl) |
| Cys(Et) | cysteinyl(S-ethyl) |
| Cys(Me) | cysteinyl(S-methyl) |
| deLeu | dehydroleucyl |
| 2,4-Diabu | 2,4-diaminobutyryl |
| 2,3-Diapr | 2,3-diaminopropionyl |
| 3,4-diFPheAla | 3-(3,4-difluorophenyl)alanyl |
| 3,4-diOMePheAla | 3-(3,4-dimethoxyphenyl)alanyl |
| Gly(Et) | N-ethylglycyl |
| Fmoc | 9-fluorenylmethyloxycarbonyl |
| 3-FPheAla | 3-(3-fluorophenyl)alanyl |
| 4-FPheAla | 3-(4-fluorophenyl)alanyl |
| Gln | glutaminyl |
| Gln(Trt) | glutaminyl(trityl) |
| Glu | glutamyl |
| Gly | glycyl |
| GlyNH$_2$ | glycylamide |
| GlyNH-ethyl | glycyl ethylamide |
| Gly(pipad) | glycyl[4-piperidinyl(N-amidino)] |
| GuaAla | 3-(guanidino)alanyl |
| 4-GuaPheAla | 3-(4-guanidinophenyl)alanyl |
| His | histidyl |
| His(Trt) | histidyl(trityl) |
| HAla | homoalanyl |
| HArg | homoarginyl |
| HIle | homoisoleucyl |
| HLeu | homoleucyl |
| HPheAla | homophenylalanyl |
| HPro | homoprolyl |
| HSer | homoseryl |
| HSer(t-Bu) | homoseryl(O-t-butyl) |
| 4-OHMePheAla | 3-(hydroxymethylphenyl)alanyl |
| OHPro | hydroxyprolyl |
| Ile | isoleucyl |
| Leu | leucyl |
| Lys | lysyl |
| Lys(Ac) | lysyl(N-epsilon-acetyl) |
| Lys(Isp) | lysyl(N-epsilon-isopropyl) |
| Lys(Nic) | lysyl(N-epsilon-nicotinyl) |
| Met | methionyl |
| Met(O$_2$) | methionyl(sulfone) |
| Met(O) | methionyl(sulfoxide) |
| N-MeAla | N-methylalanyl |
| 4-MePheAla | 3-(4-methylphenyl)alanyl |

TABLE 1-continued

| Abbreviation | Definition |
| --- | --- |
| N-MePro | N-methylprolyl |
| 1-Nal | 3-(naphth-1-yl)alanyl |
| 2-Nal | 3-(naphth-2-yl)alanyl |
| nPenGly | neopentylglycyl |
| 4-NO$_2$—PheAla | 3-(4-nitrophenyl)alanyl |
| NArg | norarginyl |
| Nle | norleucyl |
| Nva | norvalyl |
| OctylGly | octylglycyl |
| Orn | ornithyl |
| Orn(Imd) | ornithyl[N-delta-(2-imidazolinyl)] |
| Orn(Isp) | ornithyl(N-delta-isopropyl) |
| Orn(Nic) | ornithyl(N-delta-nicotinyl) |
| Pen | penicillaminyl |
| Pen(Sacme) | penicillaminyl(S-acetamidomethyl) |
| Pen(SBzl) | penicillaminyl(S-benzyl) |
| Pen(SMe) | penicillaminyl(S-methyl) |
| Arg(Pmc) | (N$^G$-2,2,5,7,8-pentamethylchroman-6-sulfonyl)arginyl |
| PheAla | phenylalanyl |
| PheGly | phenylglycyl |
| Pro | prolyl |
| ProNH-ethyl | prolyl ethylamide |
| PropGly | propargylglycyl |
| 3-Pal | 3-(3-pyridyl)alanyl |
| Glu(pyro) | pyro-glutamyl |
| (pyramid)Ala | [3-pyrrolidinyl(2-N-amidino)]alanyl |
| (pipamid)Ala | [4-piperidinyl(N-amidino)]alanyl |
| Sar | sarcosyl |
| SarNH$_2$ | sarcosylamide |
| Ser | seryl |
| SerNH$_2$ | serylamide |
| Ser(Bzl) | seryl(O-benzyl) |
| StyAla | styrylalanyl |
| Tic | 1,2,3,4-tetrahydroisoquinoline-3-carbonyl |
| 3-ThzAla | 3-(3-thiaiolyl)alanyl |
| 2-ThiAla | 3-(thien-2-yl)alanyl |
| Thr | threonyl |
| Thr(Bzl) | threonyl(O-benzyl) |
| Thr(t-Bu) | threonyl(O-t-butyl) |
| 3-CF$_3$PheAla | 3-(3-trifluoromethylphenyl)alanyl |
| 3,4,5-TriFPheAla | 3-(3,4,5-trifluorophenyl)alanyl |
| Trp |tryptyl |
| Trp(Boc) | tryptyl(N-t-butoxycarbonyl) |
| Tyr | tyrosyl |
| Tyr(t-Bu) | tyrosyl(O-t-butyl) |
| Tyr(Bzl) | tyrosyl(O-benzyl) |
| Tyr(Et) | tyrosyl(O-ethyl) |
| Val | valyl |

When not found in the table above, nomenclature and abbreviations may be further clarified by reference to the Calbiochem-Novabiochem Corp. 1999 *Catalog and Peptide Synthesis Handbook* or the Chem-Impex International, Inc. *Tools for Peptide & Solid Phase Synthesis* 1998–1999 Catalogue.

In one aspect, the present invention relates to compounds of the structure $$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} \quad (I),$$

wherein $Xaa_2$, $Xaa_3$, $Xaa_4$, $Xaa_5$, $Xaa_6$, $Xaa_7$, $Xaa_8$, $Xaa_9$, and $Xaa_{10}$ represent the residues of a peptide having nine amino acids. The N-terminus of the nonapeptide represented can be modified by an amino acyl group represented by $Xaa_1$. The group $Xaa_{11}$ represents a group suitable for modifying the C-terminus of the compound.

Suitable groups for $Xaa_1$ are hydrogen, an acyl group of the formula $R^1$—$(CH_2)_n$—$C(O)$—; wherein n is an integer from 0 to 8 and $R^1$ is selected from the group consisting of N-acetylamino, alkoxy, alkyl, aryl, carboxy, cycloalkenyl, cycloalkyl, heterocycle, and hydroxy; and an acyl group of the formula $R^2$—$CH_2CH_2$—O—$(CH_2CH_2)_p$—$CH_2$—C(O)—, wherein $R^2$ is selected from the group consisting of hydrogen, N-acetylamino, and alkyl, and p is an integer from 1 to 8. Preferred $Xaa_1$ groups for modifying the N-terminus of the compounds in the scope of the invention are acetyl and 6-methylnicotinyl.

$Xaa_2$ is an amino acyl residue selected from the group consisting of alanyl, β-alanyl, asparaginyl, citrullyl, N-ethylglycyl, glutaminyl, glutamyl, methionyl, N-methylalanyl, N-methylprolyl, prolyl, pyro-glutamyl, sarcosyl, seryl, threonyl, $H_3C$—C(O)—HN—$(CH_2)_q$—C(O)—, wherein q is 1 to 8, and $H_3C$—C(O)—HN—$CH_2CH_2$—O—$(CH_2CH_2O)_r$—$CH_2$—C(O)—, wherein r is 1 to 8; provided that when $Xaa_2$ is N-methylprolyl, $H_3C$—C(O)—HN—$(CH_2)_q$—C(O)—, or $H_3C$—C(O)—HN—$CH_2CH_2$—O—$(CH_2CH_2O)_r$—$CH_2$—C(O)—, $Xaa_1$ is absent. Preferably, $Xaa_2$ is sarcosyl.

$Xaa_3$ is an amino acyl residue selected from the group consisting of alanyl, asparaginyl, aspartyl, glutaminyl, glutamyl, glycyl, leucyl, methionyl, phenylalanyl, prolyl, and seryl. The preferred amino acid for $Xaa_3$ is glycyl.

$Xaa_4$ is an amino acyl residue selected from the group consisting of alloisoleucyl, allylglycyl, 2-aminobutyryl, (1R,4S)-1-aminocyclopent-2-ene-4-carbonyl, aspartyl, 3-(5-bromothien-2-yl)alanyl, 3-(3-chlorophenyl)alanyl, 3-(4-chlorophenyl)alanyl, 3-(3-cyanophenyl)alanyl, cysteinyl(S-ethyl), cysteinyl(S-methyl), 2,4-diaminobutanoyl, 2,3-diaminopropionyl, 3-(3,4-dimethoxyphenyl)alanyl, 3-(3-fluorophenyl)alanyl, 3-(4-fluorophenyl)alanyl, histidyl, homophenylalanyl, homoseryl, lysyl(N-epsilon-acetyl), methionyl(sulfone), methionyl(sulfoxide), 3-(4-methylphenyl)alanyl, 3-naphth-1-yl)alanyl, 3-(naphth-2-yl)alanyl, ornithyl, phenylglycyl, prolyl, 3-(3-pyridyl)alanyl, 3-(thiazolyl)alanyl, 3-(thien-2-yl)alanyl, D-3-(thien-2-yl)alanyl, seryl(O-benzyl), styrylalanyl, 1,2,3,4-tetrahydroisoquinoline-3-carbonyl, tryptyl, tyrosyl, and D-valyl. Preferred amino acyl residues for the $Xaa_4$ position include alloisoleucyl, allylglycyl, 2-aminobutyryl, (1R,4S)-1-aminocyclopent-2-ene-4-carbonyl, 3-(5-bromothien-2-yl)alanyl, 3-(3-chlorophenyl)alanyl, 3-(4-chlorophenyl)alanyl, 3-(3-cyanophenyl)alanyl, cysteinyl(S-ethyl), cysteinyl(S-methyl), 2,4-diaminobutanoyl, 2,3-diaminopropionyl, 3-(3,4-dimethoxyphenyl)alanyl, 3-(3-fluorophenyl)alanyl, 3-(4-fluorophenylalanyl), histidyl, homophenylalanyl, homoseryl, lysyl(N-epsilon-acetyl), methionyl(sulfone), methionyl(sulfoxide), 3-(4-methylphenyl)alanyl, 3-(naphth-1-yl)alanyl, 3-(naphth-2-yl)alanyl, ornithyl, phenylglycyl, prolyl, 3-(3-pyridyl)alanyl, seryl(O-benzyl), styrylalanyl, 1,2,3,4-tetrahydroisoquinoline-3-carbonyl, 3-(thiazolyl)alanyl, 3-(thien-2-yl)alanyl, D-3-(thien-2-yl)alanyl, tryptyl, tyrosyl, and D-valyl.

$Xaa_5$ is an amino acyl residue selected from the group consisting of D-alanyl, alloisoleucyl, D-alloisoleucyl, D-allothreonyl, D-allylglycyl, D-2-aminobutyryl, D-3-(4-aminophenyl)alanyl, D-asparaginyl, D-aspartyl, D-3-(4,4'-biphenyl)alanyl, D-t-butylglycyl, D-3-(4chlorophenyl)alanyl, D-3-(3-cyanophenyl)alanyl, D-citrullyl, D-cyclohexylalanyl, D-cyclohexylglycyl, D-cysteinyl, D-cysteinyl(S-t-butyl), dehydroleucyl, D-3-(3,4-difluorophenyl)alanyl, D-3-(3,4-dimethoxyphenyl)alanyl, D-glutaminyl, D-glutamyl, glycyl, D-histidyl, D-homoisoleucyl, D-homophenylalanyl, D-homoseryl, isoleucyl, D-isoleucyl, D-leucyl, D-lysyl, D-lysyl(N-epsilon-nicotinyl), D-methionyl, D-3-(4-methylphenyl)alanyl, D-3-(naphth-1-yl)alanyl, D-3-(naphth-2-yl)alanyl, D-neopentylglycyl, D-3-(4-nitrophenyl)alanyl, D-norleucyl, D-norvalyl, D-ornithyl, D-penicillaminyl, D-penicillaminyl (S-acetamidomethyl), D-penicillaminyl(S-benzyl), D-penicillaminyl(S-methyl), D-phenylalanyl, prolyl, D-prolyl, D-3-(3-pyridyl)alanyl, D-seryl, D-seryl(O-benzyl), D-3-(thien-2-yl)alanyl, D-3-(3-trifluoromethylphenyl)alanyl, D-3-(3,4,5-trifluorophenyl)alanyl, D-threonyl, D-threonyl(O-benzyl), D-tryptyl, D-tyrosyl(O-benzyl), D-tyrosyl(O-ethyl), D-tyrosyl, and D-valyl. Preferred $Xaa_5$ amino acyl residues include isoleucyl, D-isoleucyl, and D-leucyl.

$Xaa_6$ is an amino acyl selected from the group consisting of alanyl, allothreonyl, D-allothreonyl, allylglycyl, asparaginyl, cysteinyl, glutaminyl, glycyl, histidyl, homoseryl, D-homoseryl, 3-(4-hydroxymethylphenyl)alanyl, isoleucyl, lysyl(N-epsilon-acetyl), methionyl, 3-(naphth-1-yl)alanyl, 3-(naphth-2-yl)alanyl, norvalyl, octylglycyl, ornithyl, penicillaminyl, prolyl, 3-(3-pyridyl)alanyl, seryl, D-seryl, threonyl, D-threonyl, tryptyl, and tyrosyl. Preferred amino acyl residues for the $Xaa_6$ position include seryl and threonyl.

$Xaa_7$ is an amino acyl residue selected from the group consisting of alanyl, allylglycyl, 2-aminobutyryl, arginyl, asparaginyl, aspartyl, 3-(4-carboxyamidophenyl)alanyl, citrullyl, cyclohexylalanyl, cysteinyl, glutaminyl, D-glutaminyl, glutamyl, glycyl, histidyl, homoalanyl, homoleucyl, homoseryl, D-homoseryl, isoleucyl, leucyl, D-leucyl, lysyl(N-epsilon-acetyl), lysyl(N-epsilon-isopropyl), methionyl(sulfone), methionyl(sulfoxide), methionyl, 3-(naphth-1-yl)alanyl, D-3-(naphth-1-yl)alanyl, 3-(naphth-2-yl)alanyl, D-3-(naphth-2-yl)alanyl, norleucyl, norvalyl, D-norvalyl, octylglycyl, penicillaminyl, phenylalanyl, propargylglycyl, 3-(3-pyridyl)alanyl, seryl, D-seryl, threonyl, tryptyl, tyrosyl, and valyl. Preferred $Xaa_7$ amino acyl residues include glutaminyl, norvalyl, and seryl.

$Xaa_8$ is an amino acyl residue selected from the group consisting of alanyl, alloisoleucyl, D-alloisoleucyl, allylglycyl, aspartyl, t-butylglycyl, citrullyl, cyclohexylglycyl, cysteinyl, glutamyl, glycyl, homoseryl, isoleucyl, D-isoleucyl, leucyl, leucyl, lysyl(N-epsilon-acetyl), methionyl, 3-(naphth-1-yl)alanyl, 3-(naphth-2-yl)alanyl, norvalyl, penicillaminyl, phenylalanyl, prolyl, seryl, tryptyl, tyrosyl, and valyl. The preferred $Xaa_8$ amino acyl residue is isoleucyl.

$Xaa_9$ is an amino acyl residue selected from the group consisting of [(4-amino(N-isopropyl)methyl)phenyl]alanyl, 3-(4-amino-N-isopropylphenyl)alanyl, arginyl, arginyl($N^G N^{G'}$diethyl), citrullyl, 3-(cyclohexyl)alanyl(4N-isopropyl), glycyl[4-piperidinyl(N-amidino)], (3-guanidino)alanyl, 3-(4-guanidinophenyl)alanyl, histidyl, homoarginyl, lysyl, lysyl(N-epsilon-isopropyl), lysyl(N-epsilon-nicotinyl), norarginyl, ornithyl(N-delta-isopropyl), ornithyl(N-delta-nicotinyl), ornithyl[N-delta-(2-imidazolinyl)], [4-piperidinyl(N-amidino)]alanyl, and [3-pyrrolidinyl(2-N-amidino)]alanyl. The preferred $Xaa_9$ amino acyl residue is arginyl.

$Xaa_{10}$ is an amino acyl residue selected from the group consisting of D-alanyl, 2-aminobutyryl, 2-aminoisobutyryl, t-butylglycyl, homoprolyl, hydroxyprolyl, isoleucyl, leucyl, phenylalanyl, prolyl, D-prolyl, seryl, 1,2,3,4-tetrahydroisoquinoline-3-carbonyl, threonyl, and valyl. The preferred $Xaa_{10}$ amino acyl residue is prolyl.

$Xaa_{11}$ is a hydroxyl group or an amino acid amide selected from the group consisting of D-alanylamide, D-alanylethylamide, azaglycylamide, glycylamide, glycylethylamide, sarcosylamide, serylamide, and D-serylamide; or $Xaa_{11}$ is a group represented by the formula

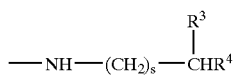

or a group represented by the formula —NH—$R^5$, wherein s is an integer selected from 0 to 8; $R^3$ is selected from hydrogen, alkyl, and a 5- to 6-membered cycloalkyl ring; $R^4$ is selected from the group consisting of hydrogen, alkoxy, alkyl, aryl, cycloalkenyl, cycloalkyl, heterocycle, and hydroxy; provided that s is not zero when $R^4$ is hydroxy or alkoxy; and $R^5$ is selected from hydrogen, hydroxy, and cycloalkyl. The preferred $Xaa_{11}$ residues include D-alanylamide and NH-ethyl.

Compositions

The compounds of the invention, including but not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. The compounds of the invention are also useful in the treatment of diseases that have angiogenesis as a pathologic consequence such as cat scratch disease (Rochele minalia quintosa) and ulcers (Helico bacterpylon). The compounds of the invention are also useful to reduce bleeding by administration prior to sugery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly (anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered together with other cytotoxic agents. In particular, when used in the treatment of solid tumors, compounds of the invention may be administered with IL-12, retinoids, interferons, angiostatin, endostatin thalidomide, thrombospondin-1, thrombospondin-2, captopryl, angioinhibins, TNP-470, pentosan polysulfate, platelet factor 4, LM-609, SU-5416, CM-101, Tecogalan, plasminogen-K-5, vasostatin, vitaxin, vasculostatin, squalamine, marimastat or othermMP inhibitors, antineoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, cisplatin, taxol, etoposide/mechlorethamine, vincristine, prednisone and procarbazine), vincristine, vinblastine, and the like as well as with radiation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, but include in principle any agents useful for the treatment or prophylaxis of angiogenic diseases.

The peptides of the invention may be used for the development of affinity columns for isolation of receptors relevant to the antiangiogenic activity of the peptide of the invention, e.g. TSP-1 receptor, in, for example, cultured endothelial cells. Isolation and purification of the receptor may be followed by amino acid sequencing to identify and isolate polynucleotides which encode the receptor. Recombinant expression of this receptor would allow greater amounts of receptor to be produced, e.g. to produce a sufficient quantity for use in high throughput screening assays to identify other angiogenesis inhibitors.

Determination of Biological Activity
In Vitro Assay for Angiogenic Activity

The human microvascular endothelial (HMVEC) migration assay was run according to the procedure of S. S. Tolsma, O. V. Volpert, D. J. Good, W. F. Frazier, P. J. Polverini and N. Bouck, J. Cell Biol. 122, 497–511 (1993).

The HMVEC migration assay was carried out using Human Microvascular Endothelial Cells-Dermal (single donor) and Human Microvascular Endothelial Cells, (neonatal). The BCE or HMVEC cells were starved overnight in DME containing 0.1% bovine serum albuminutes (BSA). Cells were then harvested with trypsin and resuspended in DME with 0.1% BSA at a concentration of $1.5 \times 10^6$ cells per mL. Cells were added to the bottom of a 48 well modified Boyden chamber (Nucleopore Corporation, Cabin John, Md.). The chamber was assembled and inverted, and cells were allowed to attach for 2 hours at 37° C. to polycarbonate chemotaxis membranes (5 mM pore size) that had been soaked in 0.1% gelatin overnight and dried. The chamber was then reinverted, and test substances (total volume of 50 $\mu$L), including activators, 15 ng/mL bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME+0.1 BSA was subtracted and the data reported as the number of cells migrated per 10 high power fields (400×) or, when results from multiple experiments were combined, as the percent inhibition of migration compared to a positive control.

Representative compounds described in Examples 1 to 50 inhibited human endothelial cell migration in the above assay by at least 50% inhibition when tested at concentrations of 1 nM. Preferred compounds inhibited human endothelial cell migration by at least 70% when tested at concentrations of 1 nM, and more preferred compounds inhibited human endothelial cell migration by at least 80% at concentrations of 1 nM.

Synthesis of the Peptides

The polypeptides of the present invention may be synthesized by many techniques that are known to those skilled in the art. For solid phase peptide synthesis, a summary of the many techniques may be found in J. M. Stewart and J. D. Young, Solid Phase Peptide Synthesis, W.H. Freeman Co. (San Francisco), 1963 and J. Meienhofer, Hormonal Proteins and Peptides, vol. 2, p. 46, Academic Press (New York) 1973. For classical solution synthesis see G. Schroder and K. Lupke, The Peptides, vol. 1, Academic Press (New York), 1965.

Reagents, resins, amino acids, and amino acid derivatives are commercially available and can be purchased from Chem-Impex International, Inc. (Wood Dale, Ill., U.S.A.) or Calbiochem-Novabiochem Corp. (San Diego, Calif., U.S.A.) unless otherwise noted herein.

In general, these methods comprise the sequential addition of one or more amino acids or suitably protected amino acids to a growing peptide chain. Normally, either the amino or carboxy group of the first amino acid is protected by a suitable nitrogen protecting group. The protected or derivatized amino acid can then be either attached to an inert solid support or utilized in solution by adding the next amino acid in the sequence having the complimentary (amino or carboxy) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the $\alpha$-amino functionality is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethoxycarbonyl (Fmoc), t-butoxycarbonyl (Boc), benzyloxycarbonyl (Cbz), biphenylisopropyloxycarbonyl, t-amyloxycarbonyl, isobornyloxycarbonyl, ($\alpha,\alpha$)-dimethyl-3,5-dimethoxybenzyloxycarbonyl, O-nitrophenylsulfenyl, 2-cyano-t-butoxycarbonyl, and the like. The 9-fluorenylmethoxycarbonyl (Fmoc) protecting group is preferred.

Particularly preferred side chain protecting groups are: for arginine and lysine: acetyl (Ac), adamantyloxycarbonyl, benzyloxycarbonyl (Cbz), t-butoxycarbonyl (Boc), 4-methoxybenzenesulfonyl, $N_G$-4-methoxy-2,3,6-trimethylbenzenesulfonyl (Mtr), 2,2,5,7,8-pentamethylchroman-6-sulfonyl (Pmc), and p-toluenesulfonyl; for asparagine: trityl (Trt); for aspatyl: t-butyl (t-Bu); for glutamyl: t-butyl (t-Bu); for glutaminyl: trityl (Trt); for histidine: trityl (Trt), benzyl, benzyloxycarbonyl (Cbz), p-toluenesulfonyl, and 2,4-dinitrophenyl; for penicillamine: methyl; for serine: t-butyl (r-Bu); for tryptophan: formyl and t-butoxycarbonyl (Boc); and for tyrosine: acetyl (Ac), benzyl, O-bromobenzyloxycarbonyl, t-butyl (t-Bu), cyclohexyl, cyclopentyl, 2,6-dichlorobenzyl, and isopropyl.

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support is Seiber ethylamide, which is commercially available from Novabiochem.

The C-terminal amino acid is coupled to the resin by means of a coupling mediated by N,N'-dicyclohexylcarbodiimide (DCC), N,N'-diisopropylcarbodiimide (DIC), O-benzotriazol-1-yl-N,N,N',N'-tetramethyluroniumhexafluorophosphate (HBTU), or [O-7-azabenzotriazol-1-yl)-1,1,3,3-tetramethyluronium hexafluorophosphate] (HATU), with or without 4-dimethylaminopyridine (DMAP), 1-hydroxybenzotriazole (HOBT), benzotriazol-1-yloxy-tris(dimethylamino) phosphoniumhexafluorophosphate (BOP), or bis(2-oxo-3-oxazolidinyl)phosphine chloride (BOPCl), for about 1 to about 24 hours at a temperature between 10° C. and 50° C. in a solvent such as dichloromethane or DMF. The Fmoc group is cleaved with a secondary amine, preferably piperidine, prior to coupling with the C-terminal amino acid as described above. The preferred method for coupling to the deprotected 4-(2',4'-dimethoxyphenyl-Fmoc-aminomethyl) phenoxyacetamidoethyl resins are O-benzotriazol-1-yl-N,N,N',N'-tetramethyluroniumhexafluorophosphate (HBTU, 1 equiv.) and 1-hydroxybenzotriazole (HOBT, 1 equiv.), or [O-(7-azabenzotriazol-1-yl)-1,1,3,3-tetramethyluronium hexafluorophosphate] (HATU, 1 equiv.) in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluronium-hexafluorophosphate (HBTU, 1 equiv.) and 1-hydroxybenzotriazole (HOBT, 1 equiv.) or [O-(7-azabenzotriazol-1-yl)-1,1,3,3-tetraethyluronium hexafluorophosphate] (HATU, 1 equiv.).

At the end of the solid phase synthesis, the polypeptide is removed from the resin and deprotected, either in succession or in a single operation. Removal of the polypeptide and deprotection can be accomplished in a single operation by treating the resin-bound polypeptide with a cleavage reagent, for example trifluoroacetic acid containing thioanisole, water, or ethanedithiol.

In cases wherein the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivitized polystyrene-divinylbenzene (for example, AMBERLITE® XAD); silica gel adsorption chromatography; ion exchange chromatography on carboxymethylcellulose; partition chromatography, e.g. on SEPHADEX® G-25, LH-20 or countercurrent distribution; high performance liquid chromatography (HPLC), especially reverse-phase HPLC on octyl- or octadecylsilyl-silica bonded phase column packing.

The foregoing may be better understood in light of the Examples which are meant to describe compounds and process which can be carried out in accordance with the invention and are not intended as a limitation on the scope of the invention in any way.

Abbreviations which have been used the following examples are: NMP for N-methylpyrrolidinone; HBTU for 2-(1H-benzotriazole-1-yl)-1,1,3,3-tetramethyluronium hexafluorophosphate; DMF for N,N-dimethylformamide, and TFA for trifluoroacetic acid.

EXAMPLE 1

N-Ac-Sar-Gly-Lys(Ac)-D-Leu-Thr-Nva-Ile-Arg-ProNH-ethyl

In the reaction vessel of an Applied Biosystems 433A peptide synthesizer was placed 0.1 mM of Fmoc-Pro-Sieber ethylamide resin. Cartridges of 1 mM amino acids were sequentially loaded. The Fastmoc 0.1 with previous peak monitoring protocol was used with the following is the synthetic cycle:

1. Resin solvated with NMP for about 5 minutes;
2. Resin washed with NMP for about 5 minutes;
3. Fmoc group removed using 50% piperidine solution in NMP for 5 minutes, resin washed, and the sequence repeated 3 to 4 times;
4. Fmoc-amino acid activated with 1 mM of 0.5M HBTU in DMF;
5. Activated Fmoc-amino acid added to the reaction vessel followed by addition of 1 mM of 2M diisopropylamine in NMP solution;
6. Fmoc-amino acid coupled for 20 minutes;
7. Resin washed and Fmoc-group removed using 50% piperidine in NMP.

The following protected amino acids were sequentially coupled to the resin using above protocol:

| Amino acid | Coupling time |
| --- | --- |
| 1. Fmoc-Arg(Pmc) | 20 minutes |
| 2. Fmoc-Ile | 20 minutes |
| 3. Fmoc-Nva | 20 minutes |
| 4. Fmoc-Thr(t-Bu) | 20 minutes |
| 5. Fmoc-D-Leu | 20 minutes |
| 6. Fmoc-Lys(Ac) | 20 minutes |
| 7. Fmoc-Gly | 20 minutes |
| 8. Fmoc-Sar | 20 minutes |
| 9. acetic acid | 20 minutes |

Upon completion of the synthesis the resin-bound peptide was washed with methanol three times and dried in vacuo, then treated with a (95:5) TFA/water solution (3 mL) at room temperature overnight. The resin was filtered and washed 3 times with methanol. The filtrates and the washes were combined and concentrated in vacuo. The residue was treated with ether and the precipitate was filtered to provide the crude peptide as an amorphous powder. This was purified by preparative HPLC using a C-18 column with a solvent system increasing in gradient from 5% to 100% acetonitrile/water containing 0.1% TFA over a period of 50 minutes. The pure fractions were lyophilized to provide N-Ac-Sar-Gly-Lys(Ac)-D-Leu-Thr-Nva-Ile-Arg-ProNHethyl as the trifluoroacetate salt; $R_t$=2.764 minutes (using a C-18 column and a solvent system increasing in gradient from 20% to 95% acetonitrile/water containing 10 mM ammonium acetate over a period of 10 minutes); MS (ESI) m/e 1065 (M+H).

EXAMPLE 2

N-Ac-Sar-Gly-Pro-D-Leu-Thr-Nva-Ile-Arg-ProNH-ethyl

The desired product was prepared by substituting Fmoc-Pro for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Pro-D-Leu-Thr-Nva-Ile-Arg-ProNH-ethyl as the trifluoroacetate salt; $R_t$=3.092 minutes (using a C-18 column and a solvent system increasing in gradient from 20% to 95% acetonitrile/water containing 10 mM ammonium acetate over a period of 10 minutes); MS (ESI) m/e 992 ($M^+$).

EXAMPLE 3

N-Ac-Sar-Gly-5-BrThiAla-D-Leu-Thr-Nva-Ile-Arg-ProNH-ethyl

The desired product was prepared by substituting Fmoc-5-BrThiAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-5-BrThiAla-D-Leu-Thr-Nva-Ile-Arg-ProNH-ethyl as the trifluoroacetate salt; $R_t$=4.392 minutes (using a C-18 column and a solvent system increasing in gradient from 20% to 95% acetonitrile/water containing 10 mM ammonium acetate over a period of 10 minutes); MS (ESI) m/e 1128 (M+H).

EXAMPLE 4

N-Ac-Sar-Gly-3-CNPheAla-D-Leu-Thr-Nva-Ile-Arg-ProNH-ethyl

The desired product was prepared by substituting Fmoc-3CNPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3-CNPheAla-D-Leu-Thr-Nva-Ile-Arg-ProNH-ethyl as the trifluoroacetate salt; $R_t$=3.805 minutes (using a C-18 column and a solvent system increasing in gradient from 20% to 95% acetonitrile/water containing 10 mM ammonium acetate over a period of 10 minutes); MS (ESI) m/e 1065 ($M^+$).

EXAMPLE 5

N-Ac-Sar-Gly-Cys(Et)-D-Leu-Thr-Nva-Ile-Arg-ProNH-ethyl

The desired product was prepared by substituting Fmoc-Cys(Et) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Cys(Et)-D-Leu-Thr-Nva-Ile-Arg-ProNH-ethyl as the trifluoroacetate salt; $R_t$=3.629 minutes (using a C-18 column and a solvent system increasing in gradient from 20% to 95% acetonitrile/water containing 10 mM ammonium acetate over a period of 10 minutes); MS (ESI) m/e 1024 ($M^+$).

EXAMPLE 6

N-Ac-Sar-Gly-3-ThzAla-D-Leu-Thr-Nva-Ile-Arg-ProNH-ethyl

The desired product was prepared by substituting Fmoc-3-ThzAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3-ThzAla-D-Leu-Thr-Nva-Ile-Arg-ProNH-ethyl as the trifluoroacetate salt; $R_t$=3.172 minutes (using a C-18 column and a solvent system increasing in gradient from 20% to 95% acetonitrile/water containing 10 mM ammonium acetate over a period of 10 minutes); MS (ESI) m/e 1049 ($M^+$).

EXAMPLE 7

N-Ac-Sar-Gly-(1R,4S)-AmCyeCO-D-Leu-Thr-Nva-Ile-Arg-ProNH-ethyl

The desired product was prepared by substituting (1R, 4S)-1-Fmoc-amino-cyclopent-2-ene-4-carboxylic acid for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-(1R,4S)-AmCyeCO-D-Leu-Thr-Nva-Ile-Arg-ProNH-ethyl as the trifluoroacetate salt; $R_t$=2.961 minutes (using a C-18 column and a solvent system increasing in gradient from 20% to 95% acetonitrile/water containing 10 mM ammonium acetate over a period of 10 minutes); MS (ESI) m/e 1004 ($M^+$).

EXAMPLE 8

N-Ac-Sar-Gly-3,4-diOMePheAla-D-Leu-Thr-Nva-Ile-Arg-ProNH-ethyl

The desired product was prepared by substituting Fmoc-3,4-diOMePheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3,4-diOMePheAla-D-Leu-Thr-Nva-Ile-Arg-ProNH-ethyl as the trifluoroacetate salt; $R_t$=3.49 minutes (using a C-18 column and a solvent system increasing in gradient from 20% to 95% acetonitrile/water containing 10 mM ammonium acetate over a period of 10 minutes); MS (ESI) m/e 1102 ($M^+$).

EXAMPLE 9

N-Ac-Sar-Gly-4-MePheAla-D-Leu-Thr-Nva-Ile-Arg-ProNH-ethyl

The desired product was prepared by substituting Fmoc-4-MePheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-4-MePheAla-D-Leu-Thr-Nva-Ile-Arg-ProNH-ethyl as the trifluoroacetate salt; $R_t$=4.2 minutes (using a C-18 column and a solvent system increasing in gradient from 20% to 95% acetonitrile/water containing 10 mM ammonium acetate over a period of 10 minutes); MS (ESI) m/e 1056 (M$^+$).

EXAMPLE 10

N-Ac-Sar-Gly-3-ClPheAla-D-Leu-Thr-Nva-Ile-Arg-ProNH-ethyl

The desired product was prepared by substituting Fmoc-3-ClPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3-ClPheAla-D-Leu-Thr-Nva-Ile-Arg-ProNH-ethyl as the trifluoroacetate salt; $R_t$=4.366 minutes (using a C-18 column and a solvent system increasing in gradient from 20% to 95% acetonitrile/water containing 10 mM ammonium acetate over a period of 10 minutes); MS (ESI) m/e 1076 (M$^+$).

EXAMPLE 11

N-Ac-Sar-Gly-2-ThiAla-D-Leu-Thr-Nva-Ile-Arg-ProNH-ethyl

The desired product was prepared by substituting Fmoc-3-(thien-2-yl)alanine for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2-ThiAla-D-Leu-Thr-Nva-Ile-Arg-ProNH-ethyl as the trifluoroacetate salt; $R_t$=3.826 minutes (using a C-18 column and a solvent system increasing in gradient from 20% to 95% acetonitrile/water containing 10 mM ammonium acetate over a period of 10 minutes); MS (ESI) m/e 1046 (M$^+$).

EXAMPLE 12

N-Ac-Sar-Gly-PheGly-D-Leu-Thr-Nva-Ile-Arg-ProNH-ethyl

The desired product was prepared by substituting Fmoc-PheGly for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-PheGly-D-Leu-Thr-Nva-Ile-Arg-ProNH-ethyl as the trifluoroacetate salt; $R_t$=3.73 minutes (using a C-18 column and a solvent system increasing in gradient from 20% to 95% acetonitrile/water containing 10 mM ammonium acetate over a period of 10 minutes); MS (ESI m/e 1026 (M$^+$).

EXAMPLE 13

N-Ac-Sar-Gly-2,4-Diabu-D-Leu-Thr-Nva-Ile-Arg-ProNH-ethyl

The desired product was prepared by substituting 4-Boc-amino-2-Fmoc-butanoic acid for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2,4-Diabu-D-Leu-Thr-Nva-Ile-Arg-ProNH-ethyl as the trifluoroacetate salt; $R_t$=2.50 minutes (using a C-18 column and a solvent system increasing in gradient from 20% to 95% acetonitrile/water containing 10 mM ammonium acetate over a period of 10 minutes); MS (ESI) m/e 995 (M$^+$).

EXAMPLE 14

N-Ac-Sar-Gly-Met(O$_2$)-D-Leu-Thr-Nva-Ile-Arg-ProNH-ethyl

The desired product was prepared by substituting Fmoc-Met(O$_2$) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Met(O$_2$)-D-Leu-Thr-Nva-Ile-Arg-ProNH-ethyl as the trifluoroacetate salt; $R_t$=2.874 minutes (using a C-18 column and a solvent system increasing in gradient from 20% to 95% acetonitrile/water containing 10 mM ammonium acetate over a period of 10 minutes); MS (ESI) m/e 1058 (M$^+$).

EXAMPLE 15

N-Ac-Sar-Gly-2-Nal-D-Leu-Thr-Nva-Ile-Arg-ProNH-ethyl

The desired product was prepared by substituting Fmoc-2-Nal for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2-Nal-D-Leu-Thr-Nva-Ile-Arg-ProNH-ethyl as the trifluoroacetate salt; $R_t$=4.56 minutes using a C-18 column and a solvent system increasing in gradient from 20% to 95% acetonitrile/water containing 10 mM ammonium acetate over a period of 10 minutes); MS (ESI) m/e 1092 (M$^+$).

EXAMPLE 16

N-Ac-Sar-Gly-1-Nal-D-Leu-Thr-Nva-Ile-Arg-ProNH-ethyl

The desired product was prepared by substituting Fmoc-1-Nal for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-1-Nal-D-Leu-Thr-Nva-Ile-Arg-ProNH-ethyl as the trifluoroacetate salt; $R_t$=4.558 minutes (using a C-18 column and a solvent system increasing in gradient from 20% to 95% acetonitrile/water containing 10 mM ammonium acetate over a period of 10 minutes); MS (ES) m/e 1092 (M$^+$).

EXAMPLE 17

N-Ac-Sar-Gly-2-Abu-D-Leu-Thr-Nva-Ile-Arg-ProNH-ethyl

The desired product was prepared by substituting Fmoc-2-Abu for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2-Abu-D-Leu-Thr-Nva-Ile-Arg-ProNH-ethyl as the trifluoroacetate salt; $R_t$=3.181 minutes (using a C-18 column and a solvent system increasing in gradient from 20% to 95% acetonitrile/water containing 10 mM ammonium acetate over a period of 10 minutes); MS (ESI) m/e 980 (M$^+$).

EXAMPLE 18

N-Ac-Sar-Gly-Met(O)D-Leu-Thr-Nva-Ile-Arg-ProNH-ethyl

The desired product was prepared by substituting Fmoc-Met(O) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Met(O)-D-Leu-Thr-Nva-Ile-Arg-ProNH-ethyl as the trifluoroacetate salt; $R_t$=2.543 minutes (using a C-18 column and a solvent system increasing in gradient from 20% to 95% acetonitrile/water containing 10 mM ammonium acetate over a period of 10 minutes); MS (ESI) m/e 1042 (M$^+$).

EXAMPLE 19

N-Ac-Sar-Gly-Orn-D-Leu-Thr-Nva-Ile-Arg-ProNH-ethyl

The desired product was prepared by substituting Fmoc-α-amino-Boc-δ-amino Orn for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Orn-D-Leu-Thr-Nva-Ile-Arg-ProNH-ethyl as the trifluoroacetate salt; $R_t$=2.455 minutes (using a C-18 column and a solvent system increasing in gradient from 20% to 95% acetonitrile/water containing 10 mM ammonium acetate over a period of 10 minutes); MS (ESI) m/e 1009 (M$^+$).

EXAMPLE 20

N-Ac-Sar-Gly-His-D-Leu-Thr-Nva-Ile-Arg-ProNH-ethyl

The desired product was prepared by substituting Fmoc-His(Trt) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-His-D-Leu-Thr-Nva-Ile-Arg-ProNH-ethyl as the trifluoroacetate salt; $R_t$=2.508 minutes (using a C-18 column and a solvent system increasing in gradient from 20% to 95% acetonitrile/water containing 10 mM ammonium acetate over a period of 10 minutes); MS (ESI) m/e 1032 (M$^+$).

EXAMPLE 21

N-Ac-Sar-Gly-Trp-D-Leu-Thr-Nva-Ile-Arg-ProNH-ethyl

The desired product was prepared by substituting Fmoc-Trp(Boc) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Trp-Leu-Thr-Nva-Ile-Arg-ProNH-ethyl as the trifluoroacetate salt; $R_t$=3.912 minutes (using a C-18 column and a solvent system increasing in gradient from 20% to 95% acetonitrile/water containing 10 mM ammonium acetate over a period of 10 minutes); MS (ESI) m/e 1081 (M$^+$).

EXAMPLE 22

N-Ac-Sar-Gly-4-ClPheAla-D-Leu-Thr-Nva-Ile-Arg-ProNH-ethyl

The desired product was prepared by substituting Fmoc-4-ClPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-4-ClPheAla-D-Leu-Thr-Nva-Ile-Arg-ProNH-ethyl as the trifluoroacetate salt; $R_t$=4.089 minutes (using a C-18 column and a solvent system increasing in gradient from 20% to 95% acetonitrile/water containing 10 mM ammonium acetate over a period of 10 minutes); MS (ESI) m/e 1076 (M$^+$).

EXAMPLE 23

N-Ac-Sar-Gly-HPheAla-D-Leu-Thr-Nva-Ile-Arg-ProNH-ethyl

The desired product was prepared by substituting Fmoc-HPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-HPheAla-D-Leu-Thr-Nva-Ile-Arg-ProNH-ethyl as the trifluoroacetate salt; $R_t$=4.265 minutes (using a C-18 column and a solvent system increasing in gradient from 20% to 95% acetonitrile/water containing 10 mM ammonium acetate over a period of 10 minutes); MS (ESI) m/e 1056 (M$^+$).

EXAMPLE 24

N-Ac-Sar-Gly-Tic-D-Leu-Thr-Nva-Ile-Arg-ProNH-ethyl

The desired product was prepared by substituting Fmoc-Tic for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Tic-D-Leu-Thr-Nva-Ile-Arg-ProNH-ethyl as the trifluoroacetate salt; $R_t$=4.155 minutes (using a C-18 column and a solvent system increasing in gradient from 20% to 95% acetonitrile/water containing 10 mM ammonium acetate over a period of 10 minutes); MS (ESI) m/e 1054 (M$^+$).

EXAMPLE 25

N-Ac-Sar-Gly-StyAla-D-Leu-Thr-Nva-Ile-Arg-ProNH-ethyl

The desired product was prepared by substituting Fmoc-StyAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-StyAla-D-Leu-Thr-Nva-Ile-Arg-ProNH-ethyl as the trifluoroacetate salt; $R_t$=4.475 minutes (using a C-18 column and a solvent system increasing in gradient from 20% to 95% acetonitrile/water containing 10 mM ammonium acetate over a period of 10 minutes); MS (ESI) m/e 1068 (M$^+$).

EXAMPLE 26

N-Ac-Sar-Gly-Cys(Me)-D-Leu-Thr-Nva-Ile-Arg-ProNH-ethyl

The desired product was prepared by substituting Fmoc-Cys(Me) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Cys(Me)-D-Leu-Thr-Nva-Ile-Arg-ProNH-ethyl as the trifluoroacetate salt; $R_t$=4.045 minutes (using a C-18 column and a solvent system increasing in gradient from 20% to 95% acetonitrile/water containing 10 mM ammonium acetate over a period of 10 minutes); MS (ESI) m/e 1087 (M$^+$).

EXAMPLE 27

N-Ac-Sar-Gly-AllylGly-D-Leu-Thr-Nva-Ile-Arg-ProNH-ethyl

The desired product was prepared by substituting Fmoc-AllylGly for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-AllylGly-D-Leu-Thr-Nva-Ile-Arg-ProNH-ethyl as the trifluoroacetate salt; $R_t$=3.33 minutes (using a C-18 column and a solvent system increasing in gradient from 20% to 95% acetonitrile/water containing 10 mM ammonium acetate over a period of 10 minutes); MS (ESI) m/e 992 (M$^+$).

EXAMPLE 28

N-Ac-Sar-Gly-Cys(Et)-D-Leu-Thr-Nva-Ile-Arg-ProNH-ethyl

The desired product was prepared by substituting Fmoc-Cys(Et) for Fmoc-Lys(Ac) in Example 1. Upon completion of the synthesis, cleavage of the peptide from the resin, removal of the protecting groups, precipitation with diethyl ether, and filtration, the crude peptide was obtained This was purified by preparative HPLC to provide N-Ac-Sar-Gly-Cys(Et)-D-Leu-Thr-Nva-Ile-Arg-ProNH-ethyl as the trifluoroacetate salt; $R_t$=3.629 minutes (using a C-18 column and a solvent system increasing in gradient from 20% to 95% acetonitrile/water containing 10 mM ammonium acetate over a period of 10 minutes); MS (ESI) m/e 1026 (M$^+$).

EXAMPLE 29

N-Ac-Sar-Gly-4-FPheAla-D-Leu-Thr-Nva-Ile-Arg-ProNH-ethyl

The desired product was prepared by substituting Fmoc-4-FPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-4-FPheAla-D-Leu-Thr-Nva-Ile-Arg-ProNH-ethyl as the trifluoroacetate salt; $R_t$=4.053 minutes (using a C-18 column and a solvent system increasing in gradient from 20% to 95% acetonitrile/water containing 10 mM ammonium acetate over a period of 10 minutes); MS (ESI) m/e 1060 (M$^+$).

EXAMPLE 30

N-Ac-Sar-Gly-2,3-Diapr-D-Leu-Thr-Nva-Ile-Arg-ProNH-ethyl

The desired product was prepared by substituting Fmoc-α-amino-β-aminopropionic acid for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2,3-Diapr-D-Leu-Thr-Nva-Ile-Arg-ProNH-ethyl as the trifluoroacetate salt; $R_t$=2.529 minutes (using a C-18 column and a solvent system increasing in gradient from 20% to 95% acetonitrile/water containing 10 mM ammonium acetate over a period of 10 minutes); MS (ESI) m/e 981 (M$^+$).

EXAMPLE 31

N-Ac-Sar-Gly-Tyr-D-Ile-Thr-Nva-Ile-Arg-ProNH-ethyl

The desired product was prepared by substituting Fmoc-Tyr(t-Bu) for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Tyr-D-Ile-Thr-Nva-Ile-Arg-ProNH-ethyl as the trifluoroacetate salt; $R_t$=2.99 minutes (using a C-18 column and a solvent system increasing in gradient from 20% to 95% acetonitrile/water containing 10 mM ammonium acetate over a period of 10 minutes); MS (ESI) m/e 1058 (M+H).

EXAMPLE 32

N-Ac-Sar-Gly-Met($O_2$)-D-Ile-Thr-Nva-Ile-Arg-ProNH-ethyl

The desired product was prepared by substituting Fmoc-Met($O_2$) for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Met($O_2$)-D-Ile-Thr-Nva-Ile-Arg-ProNH-ethyl as the trifluoroacetate salt; $R_t$=2.64 minutes (using a C-18 column and a solvent system increasing in gradient from 20% to 95% acetonitrile/water containing 10 mM ammonium acetate over a period of 10 minutes); MS (ESI) m/e 1058 (M+H); Amino Acid Anal.: 0.98 Sar; 0.94 Gly; 0.90 Met($O_2$); 2.04 Ile; 0.59 Thr; 0.97 Nva; 1.32 Arg; 1.07 Pro.

EXAMPLE 33

N-Ac-Sar-Gly-3-Pal-D-Ile-Thr-Nva-Ile-Arg-ProNH-ethyl

The desired product was prepared by substituting Fmoc-3-Pal for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3-Pal-D-Ile-Thr-Nva-Ile-Arg-ProNH-ethyl as the trifluoroacetate salt; $R_t$=2.79 minutes (using a C-18 column and a solvent system increasing in gradient from 20% to 95% acetonitrile/water containing 10 mM ammonium acetate over a period of 10 minutes); MS (ESI) m/e 1043 (M+H); Amino Acid Anal.: 1.00 Sar, 0.95 Gly; 0.89 3Pal; 2.05 Ile; 0.55 Thr; 0.99 Nva; 1.43 Arg; 1.08 Pro.

EXAMPLE 34

N-Ac-Sar-Gly-4-ClPheAla-D-Ile-Thr-Nva-Ile-Arg-ProNH-ethyl

The desired product was prepared by substituting Fmoc-4-ClPheAla for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-4-ClPheAla-D-Ile-Thr-Nva-Ile-Arg-ProNH-ethyl as the trifluoroacetate salt; $R_t$=4.17 minutes (using a C-18 column and a solvent system increasing in gradient from 20% to 95% acetonitrile/water containing 10 mM ammonium acetate over a period of 10 minutes); MS (ESI) m/e 1076 (M+H); Amino Acid Anal.: 0.97 Sar; 0.96 Gly; 1.20 4ClPheAla; 2.08 Ile; 0.49 Thr; 0.96 Nva; 1.39 Arg; 1.07 Pro.

EXAMPLE 35

N-Ac-Sar-Gly-1-Nal-D-Ile-Thr-Nva-Ile-Arg-ProNH-ethyl

The desired product was prepared by substituting Fmoc-1-Nal for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-1-Nal-D-Ile-Thr-Nva-Ile-Arg-ProNH-ethyl as the trifluoroacetate salt; $R_t$=4.34 minutes (using a C-18 column and a solvent system increasing in gradient from 20% to 95% acetonitrile/water containing 10 mM ammonium acetate over a period of 10 minutes); MS (ESI) m/e 1092 (M+H); Amino Acid Anal.: 1.06 Sar; 0.96 Gly; 2.09 Ile; 0.48 Thr; 1.00 Nva; 1.41 Arg; 1.01 Pro.

EXAMPLE 36

N-Ac-Sar-Gly-2-Nal-D-Ile-Thr-Nva-Ile-Arg-ProNH-ethyl

The desired product was prepared by substituting Fmoc-2-Nal for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-2-Nal-D-Ile-Thr-Nva-Ile-Arg-ProNH-ethyl as the trifluoroacetate salt; $R_t$=4.36 minutes (using a C-18 column and a solvent system increasing in gradient from 20% to 95% acetonitrile/water containing 10 mM ammonium acetate over a period of 10 minutes); MS (ESI) m/e 1092 (M+H); Amino Acid Anal.: 0.94 Sar; 0.97 Gly; 2.05 Ile; 0.56 Thr; 0.97 Nva; 1.38 Arg; 1.08 Pro.

EXAMPLE 37

N-Ac-Sar-Gly-3-FPheAla-D-Ile-Thr-Nva-Ile-Arg-ProNH-ethyl

The desired product was prepared by substituting Fmoc-3FPheAla for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3-FPheAla-D-Ile-Thr-Nva-Ile-Arg-ProNH-ethyl as the trifluoroacetate salt; $R_t$=3.78 minutes (using a C-18 column and a solvent system increasing in gradient from 20% to 95% acetonitrile/water containing 10 mM ammonium acetate over a period of 10 minutes); MS (ESI) m/e 1060 (M+H); Amino Acid Anal.: 1.06 Sar, 0.96 Gly; 1.04 3FPheAla; 2.01 Ile; 0.47 Thr, 1.00 Nva; 1.41 Arg; 1.03 Pro.

EXAMPLE 38

N-Ac-Sar-Gly-HPheAla-D-Ile-Thr-Nva-Ile-Arg-ProNH-ethyl

The desired product was prepared by substituting Fmoc-HPheAla for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-HPheAla-D-Ile-Thr-Nva-Ile-Arg-ProNH-ethyl as the trifluoroacetate salt; $R_t$=3.70 minutes (using a C-18 column and a solvent system increasing in gradient from 20% to 95% acetonitrile/water containing 10 mM ammonium acetate over a period of 10 minutes); MS (ESI) m/e 1056 (M+H); Amino Acid Anal.: 1.01 Sar; 0.97 Gly; 1.09 HPheAla; 2.11 Ile; 0.49 Thr; 1.03 Nva; 1.39 Arg; 1.09 Pro.

EXAMPLE 39

N-Ac-Sar-Gly-4-FPheAla-D-Ile-Thr-Nva-Ile-Arg-ProNH-ethyl

The desired product was prepared by substituting Fmoc-4-FPheAla for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-4-FPheAla-D-Ile-Thr-Nva-Ile-Arg-ProNH-ethyl as the trifluoroacetate salt; $R_t$=3.89 minutes (using a C-18 column and a solvent system increasing in gradient from 20% to 95% acetonitrile/water containing 10 mM ammonium acetate over a period of 10 minutes); MS (ESI) m/e 1060 (M+H); Amino Acid Anal.: 0.97 Sar, 0.97 Gly; 0.46 4FPheAla; 1.73 Ile; 0.49 Thr, 1.01 Nva; 1.45 Arg; 1.03 Pro.

EXAMPLE 40

N-Ac-Sar-Gly-alloIle-D-Ile-Thr-Nva-Ile-Arg-ProNH-ethyl

The desired product was prepared by substituting Fmoc-alloIle for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-alloIle-D-Ile-Thr-Nva-Ile-Arg-ProNH-ethyl as the trifluoroacetate salt; $R_t$=3.44 minutes (using a C-18 column and a solvent system increasing in gradient from 20% to 95% acetonitrile/water containing 10 mM ammonium acetate over a period of 10 minutes); MS (ESI) m/e 1008 (M+H); Amino Acid Anal.: 1.08 Sar; 0.98 Gly; 2.99 Ile; 0.54 Thr; 1.02 Nva; 1.45 Arg; 1.02 Pro.

EXAMPLE 41

N-Ac-Sar-Gly-Ser(Bzl)-D-Leu-Thr-Nva-Ile-Arg-ProNH-ethyl

The desired product was prepared by substituting Fmoc-Ser(Bzl) for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-Ser(Bzl)-D-Leu-Thr-Nva-Ile-Arg-ProNH-ethyl as the trifluoroacetate salt; $R_t$=4.171 minutes (using a C-18 column and a solvent system increasing in gradient from 20% to 95% acetonitrile/water containing 10 mM ammonium acetate over a period of 10 minutes); MS (ESI) m/e 1070 ($M^+$).

EXAMPLE 42

N-Ac-Sar-Gly-HSer-D-Ile-Thr-Nva-Ile-Arg-ProNH-ethyl

The desired product was prepared by substituting Fmoc-HSer(t-Bu) for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-HSer-D-De-Thr-Nva-Ile-Arg-ProNH-ethyl as the trifluoroacetate salt; $R_t$=2.4 minutes (using a C-18 column and a solvent system increasing in gradient from 20% to 95% acetonitrile/water containing 10 mM ammonium acetate over a period of 10 minutes); MS (ESI) m/e 996 (M+H); Amino Acid Anal.: 1.01 Sar; 0.97 Gly; 0.43 HSer, 2.03 Ile; 0.55 Thr, 0.94 Nva; 1.31 Arg; 1.04 Pro.

EXAMPLE 43

N-Ac-Sar-Gly-(1R,4S)-AmCyeCO-D-Leu-Ser-Ser-Ile-Arg-ProNH-ethyl

The desired product was prepared by substituting Fmoc-(1R,4S)-AmCyeCO for Fmoc-Lys(Ac), Fmoc-Ser(t-Bu) for Fmoc-Thr(t-Bu) and Fmoc-Ser(t-Bu) for Fmoc-Nva in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-(1R,4S)-AmCyeCO-D-Leu-Ser-Ser-Ile-Arg-ProNH-ethyl as the trifluoroacetate salt; $R_t$=2.69 minutes (using a C-18 column and a solvent system increasing in gradient from 20% to 95% acetonitrile/water containing 10 mM ammonium acetate over a period of 10 minutes); MS (ESI) m/e 978 $(M+H)^+$; Amino Acid Anal.: 1.02 Sar, 0.96 Gly; 1.04 Leu; 1.01 Ile; 0.79 Ser; 1.00 Arg; 1.03 Pro.

EXAMPLE 44

N-(6-MeNicotinyl)-Sar-Gly-(1R,4S)-AmCyeCO-Leu-Thr-Nva-Ile-Arg-ProNH-ethyl

The desired product was prepared by substituting 6-methylnicotinic acid for acetic acid and Fmoc-(1R,4S)-AmCyeCO for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-(6-MeNicotinyl)-Sar-Gly-(1R,4S)-AmCyeCO-D-Leu-Thr-Nva-Ile-Arg-ProNH-ethyl as the trifluoroacetate salt; $R_t$=3.67 minutes (using a C-18 column and a solvent system increasing in gradient from 20% to 95% acetonitrile/water containing 10 mM ammonium acetate over a period of 10 minutes); MS (ESI) m/e 1081 $(M+H)^+$; Amino Acid Anal.: 0.98 Sar; 0.97 Gly; 1.02 Leu; 0.51 Thr; 1.03 Nva; 1.01 Ile; 1.05 Arg; 1.02 Pro.

EXAMPLE 45

N-Ac-Sar-Gly-D-ThiAla-D-Leu-Thr-Nva-Ile-Arg-ProNH-ethyl

The desired product was prepared by substituting Fmoc-D-ThiAla for Fmoc-Lys(Ac) in example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-D-ThiAla-D-Leu-Thr-Nva-Ile-Arg-ProNH-ethyl as the trifluoroacetate salt; $R_t$=4.03 minutes (using a C-18 column and a solvent system increasing in gradient from 20% to 95% acetonitrile/water containing 10 mM ammonium acetate over a period of 10 minutes); MS (ESI) m/e 1048 $(M+H)^+$; Amino Acid Anal.: 0.99 Sar; 0.94 Gly; 1.02 Leu; 0.45 Thr, 0.99 Nva; 1.03 Ile; 1.01 Arg; 1.00 Pro.

EXAMPLE 46

N-Ac-Sar-Gly-3CNPheAla-D-Leu-Thr-Nva-Ile-Arg-Pro-DAlaNH$_2$

The desired product was prepared by substituting Fmoc-DAla-Sieber amide resin for Fmoc-Pro-Sieber ethylamide resin and Fmoc-3CNPheAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-3CNPheAla-D-Leu-Thr-Nva-Ile-Arg-ProNH-ethyl as the trifluoroacetate salt; $R_t$=3.83 minutes (using a C-18 column and a solvent system increasing in gradient from 20% to 95% acetonitrile/water containing 10 mM ammonium acetate over a period of 10 minutes); MS (ESI) m/e 1110 $(M+H)^+$; Amino Acid Anal.: 1.02 Sar; 0.98 Gly; 0.96 Leu; 0.48 Thr; 1.01 Nva; 0.99 Ile; 1.04 Arg; 1.1 Pro; 1.03 Ala.

EXAMPLE 47

N-Ac-Sar-Gly-D-Val-D-Ile-Thr-Nva-Ile-Arg-ProNHEt

The desired product was prepared by substituting Fmoc-D-Val for Fmoc-Lys(Ac) and Fmoc-D-Ile for Fmoc-D-Leu in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-D-Val-D-Ile-Thr-Nva-Ile-Arg-ProNHEt as the trifluoroacetate salt; $R_t$=3.31 minutes (using a C-18 column and a solvent system increasing in gradient from 20% to 95% acetonitrile/water containing 10 mM ammonium acetate over a period of 10 minutes); MS (ESI) m/e 994 (M+H)⁺; Amino Acid Anal.: 1.02 Sar; 0.98 Gly; 1.00 Val; 2.10 Be; 0.44 Thr; 1.03 Nva; 0.93 Arg; 1.03 Pro.

EXAMPLE 48

N-Ac-Sar-Gly-ThiAla-D-Leu-Thr-Nva-Ile-Arg-Pro-D-AlaNH$_2$

The desired product was prepared by substituting Fmoc-DAla-Sieber amide resin for Fmoc-Pro-Sieber ethylamide resin and Fmoc-ThiAla for Fmoc-Lys(Ac) in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-ThiAla-D-Leu-Thr-Nva-Ile-Arg-Pro-DAlaNH$_2$ as the trifluoroacetate salt; R$_t$=3.77 minutes (using a C-18 column and a solvent system increasing in gradient from 20% to 95% acetonitrile/water containing 10 mM ammonium acetate over a period of 10 minutes); MS (ESI) m/e 1091 (M+H)⁺; Amino Acid Anal.: 0.96 Sar; 1.03 Gly; 1.02 Leu; 0.43 Thr; 1.02 Nva; 0.97 Ile; 1.00 Arg; 1.08 Pro.

EXAMPLE 49

N-Ac-Sar-Gly-(1R,4S)-AmCyeCO-D-Leu-Thr-Gln-Ile-Arg-ProNH-ethyl

The desired product was prepared by substituting Fmoc-(1R,4S)-AmCyeCO for Fmoc-Lys(Ac) and Fmoc-Gln(Trt) for Fmoc-Nva in Example 1. Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-(1R,4S)-AmCyeCO-D-Leu-Thr-Gln-Ile-Arg-ProNH-ethyl as the trifluoroacetate salt; R$_t$=2.78 minutes (using a C-18 column and a solvent system increasing in gradient from 20% to 95% acetonitrile/water containing 10 mM ammonium acetate over a period of 10 minutes); MS (ESI) m/e 1033 (M⁺); Amino Acid Anal.: 1.00 Sar, 1.02 Gly; 1.08 Leu; 0.58 Thr; 0.98 Glu; 1.01 Ile; 1.00 Arg; 1.01 Pro.

EXAMPLE 50

N-Ac-Sar-Gly-D-Val-Ile-Thr-Nva-Ile-Arg-ProNH-ethyl

The desired product was prepared by substituting Fmoc-D-Val for Fmoc-Lys(Ac) and Fmoc-Ile for Fmoc-D-Leu in Example 1 Upon completion of the synthesis, cleavage of the peptide from the resin, removal of the protecting groups, precipitation with diethyl ether, and filtration, the crude peptide was obtained. This was purified by preparative HPLC to provide N-Ac-Sar-Gly-D-Val-Ile-Thr-Nva-Ile-Arg-ProNH-ethyl as the trifluoroacetate salt; R$_t$=3.90 minutes (using a C-18 column and a solvent system increasing in gradient from 20% to 95% acetonitrile/water containing 10 mM ammonium acetate over a period of 10 minutes); MS (ESI) m/e 993 (M⁺); Amino Acid Anal.: 0.94 Sar; 0.97 Gly; 1.07 Val; 1.88 Ile; 0.51 Thr; 1.10 Nva; 1.02 Arg; 1.06 Pro.

It will be evident to one skilled in the art that the instant invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A compound of formula (I)

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} (I),$$

or a pharmaceutically acceptable salt thereof, wherein $Xaa_1$ is an acyl group, wherein the acyl group is selected from the group consisting of $R^1$—$(CH_2)_n$—$C(O)$—, wherein n is an integer from 0 to 8 and $R^1$ is selected from the group consisting of N-acetylamino, alkoxy, alkyl, aryl, carboxy, cycloalkenyl, cycloalkyl, heterocycle, hydroxy; and $R^2$—$CH_2CH_2$—$O$—$(CH_2CH_2O)_p$—$CH_2$—$(O)$—, wherein p is an integer from 1 to 8 and $R^2$ is selected from the group consisting of hydrogen, N-acetylamino, and alkyl;

$Xaa_2$ is an amino acyl residue selected from the group consisting of alanyl,
β-alanyl,
asparaginyl,
citrullyl,
N-ethylglycyl,
glutaminyl,
glutamyl,
methionyl,
asparaginyl,
aspartyl,
glutaminyl,
glutamyl,
glycyl,
leucyl,
methionyl,
phenylalanyl, prolyl, and
seryl;
Xaa₄ is an amino acyl residue selected from the group consisting of
  alloisoleucyl,
  allylglycyl,
  2-aminobutyryl,
  (1R,4S)-1-aminocyclopent-2-ene-4-carbonyl,
  aspartyl,
  3-(5-bromothien-2-yl)alanyl,
  3-(3-chlorophenyl)alanyl,
  3-(4-chlorophenyl)alanyl,
  ornithyl,
  phenylglycyl,
  prolyl,
  3-(3-pyridyl)alanyl,
  seryl(benzyl),
  styrylalanyl,
  1,2,3,4-tetrahydroisoquinoline-3-carbonyl,
  3-(thiazolyl)alanyl,
  3-(thien-2-yl)alanyl,
  D-3-(thien-2-yl)alanyl,
  tryptyl,
  tyrosyl, and
  D-valyl;
Xaa₅ is an amino acyl residue selected from the group consisting of
  D-alanyl,
  alloisoleucyl,
  D-alloisoleucyl,
  D-allylglycyl,
  D-2-aminobutyryl,
  D-3-(4-aminophenyl)alanyl,
  D-asparaginyl,
  D-aspartyl,
  D-3-(4,4'-biphenyl)alanyl,
  D-t-butylglycyl,
  D-3-(4-chlorophenyl)alanyl,
  D-citrullyl,
  D-3-(3-cyanophenyl)alanyl,
  D-cyclohexylalanyl,
  D-cyclohexylglycyl,
  D-cysteinyl,
  D-cysteinyl(S-t-butyl),
  dehydroleucyl,
  D-3-(3,4-difluorophenyl)alanyl,
  D-3-(3,4-dimethoxyphenyl)alanyl,
  D-glutaminyl,
  D-glutamyl,
  glycyl,
  D-histidyl,
  D-homoisoleucyl,
  D-homophenylalanyl,
  D-homoseryl,
  isoleucyl,
  D-isoleucyl,
  D-leucyl,
  D-lysyl,
  D-lysyl(N-epsilon-nicotinyl),
  D-methionyl,
  D-3-(4-methylphenyl)alanyl,
  D-3-(naphth-1-yl)alanyl,
  D-3-(naphth-2-yl)alanyl,
  D-neopentylglycyl,
  D-3-(4-nitrophenyl)alanyl,
  D-norleucyl,
  D-norvalyl,
  D-ornithyl,
  D-penicillaminyl,
  D-penicillaminyl(S-acetamidomethyl),
  D-penicillaminyl(S-benzyl),
  D-penicillaminyl(S-methyl),
  D-phenylalanyl,
  prolyl,
  D-prolyl,
  D-3-(3-pyridyl)alanyl,
  D-seryl,
  D-seryl(O-benzyl),
  D-3-(thien-2-yl)alanyl,
  D-threonyl,
  D-threonyl(O-benzyl),
  D-3-(3-trifluoromethylphenyl)alanyl,
  D-3-(3,4,5-trifluorophenyl)alanyl,
  D-tryptyl,
  D-tyrosyl(O-benzyl),
  D-tyrosyl(O-ethyl),
  D-tyrosyl, and
  D-valyl;
Xaa₆ is an amino acyl residue selected from the group consisting of
  alanyl,
  allothreonyl,
  D-allothreonyl,
  allylglycyl,
  asparaginyl,
  cysteinyl,
  glutaminyl,
  glycyl,
  histidyl,
  homoseryl,
  D-homoseryl,
  3-(4-hydroxymethylphenyl)alanyl,
  isoleucyl,
  lysyl(N-epsilon-acetyl),
  methionyl,
  3-(naphth-2-yl)alanyl,
  norvalyl,
  octylglycyl,
  ornithyl,
  penicillaminyl,
  prolyl,
  3-(3-pyridyl)alanyl,
  seryl,
  D-seryl,
  threonyl,
  D-threonyl,
  tryptyl, and
  tyrosyl;
Xaa₇ is an amino acyl residue selected from the group consisting of
  alanyl,
  allylglycyl,
  2-aminobutyryl,
  arginyl,
  asparaginyl,
  aspartyl,
  3-(4-carboxyamidophenyl)alanyl,
  citrullyl,
  cyclohexylalanyl,
  cysteinyl,
  glutaminyl,
  D-glutaminyl,
  glutamyl,
  glycyl,
  histidyl, homoalanyl,
homoleucyl,
homoseryl,
D-homoseryl,
isoleucyl,
leucyl,
D-leucyl,
3-(3-pyridyl)alanyl,
seryl,
D-seryl,
threonyl,
tryptyl,
tyrosyl, and
valyl;

$Xaa_8$ is an amino acyl residue selected from the group consisting of
alanyl,
alloisoleucyl,
D-alloisoleucyl,
allylglycyl,
aspartyl,
t-butylglycyl,
citrullyl,
cyclohexylglycyl,
cysteinyl,
glutamyl,
glycyl,
homoseryl,
isoleucyl,
D-isoleucyl,
leucyl,
lysyl(N-epsilon-acetyl),
methionyl,
3-(naphth-1-yl)alanyl,
3-(naphth-2-yl)alanyl,
norvalyl,
penicillaminyl,
phenylalanyl,
prolyl,
seryl,
tryptyl,
tyrosyl, and
valyl;

$Xaa_9$ is an amino acyl residue selected from
[(4-amino(N-isopropyl)methyl)phenyl]alanyl,
3-(4-amino-N-isopropylphenyl)alanyl,
arginyl,
arginyl($N^G N^{G'}$diethyl),
citrullyl,
3-(cyclohexyl)alanyl(4-N-isopropyl),
glycyl[4-piperidinyl(N-amidino)],
(3-guanidino)alanyl,
3-(4-guanidinophenyl)alanyl,
histidyl,
homoarginyl,
lysyl,
lysyl(N-epsilon-isopropyl),
lysyl(N-epsilon-nicotinyl),
norarginyl,
ornithyl(N-delta-isopropyl),
ornithyl(N-delta-nicotinyl),
ornithyl[N-delta-(2-imidazolinyl)],
[4-piperidinyl(N-amidino)]alanyl, and
[3-pyrrolidinyl(2-N-amidino)]alanyl;

$Xaa_{10}$ is an amino acyl residue selected from the group consisting of
D-alanyl,
2-aminobutyryl,
2-aminoisobutyryl,
t-butylglycyl,
homoprolyl,
hydroxyprolyl,
isoleucyl,
leucyl,
phenylalanyl,
prolyl,
D-prolyl,
seryl,
1,2,3,4-tetrahydroisoquinoline-3-carbonyl,
threonyl, and
valyl;

$Xaa_{11}$ is a hydroxy group or an amino acid amide selected from the group consisting of
D-alanylamide,
D-alanylethylamide,
azaglycylamide,
glycylamide,
glycylethylamide,
sarcosylamide,
serylamide,
D-serylamide,
a residue represented by the formula $$-NH-(CH_2)_s-\overset{R^3}{\underset{|}{C}}HR^4, \text{ and}$$

a group represented by the formula $-NH-R^5$;
wherein
s is an integer selected from 0 to 8;
$R^3$ is selected from the group consisting of hydrogen, alkyl, and a 5- to 6-membered cycloalkyl ring,
$R^4$ is selected from the group consisting of hydrogen, alkoxy, alkyl, aryl, cycloalkenyl, cycloalkyl, heterocycle, and hydroxy;
provided that s is not zero when $R^4$ is hydroxy or alkoxy; and
$R^5$ is selected from hydrogen, hydroxy, and cycloalkyl.

2. A compound according to claim 1, wherein is selected from the group consisting of
acetyl,
N-acetyl-β-alanyl,
(4-N-acetylamino)butyryl,
(6-N-acetylamino)caproyl,
(8-N-acetylamino)-3,6-dioxo-octanoyl,
butyryl,
caproyl,
5-chloro-2-hydroxynicotinyl,
5-chloro-6-hydroxynicotinyl,
2-chloroisonicotinyl,
2-chloro-6-methylnicotinyl,
cyclohexylacetyl,
furoyl,
2-hydroxy-6-methylnicotinyl,
6-hydroxynicotinyl,
6-hydroxy-2-picolinyl,
isonicotinyl, 2-methoxyacetyl,
2-methylnicotinyl,
6-methylnicotinyl,
(4-methyl)phenylacetyl,
nicotinyl,
phenylacetyl,
propionyl,
shikimyl,
succinyl, and
tetrahydrofuroyl.

3. A compound according to claim 2 wherein $Xaa_1$ is selected from the group consisting of
acetyl, and
6-methylnicotinyl.

4. A compound according to claim 1 wherein $Xaa_2$ is selected from the group consisting of
alanyl,
β-alanyl,
asparaginyl,
citrullyl,
N-ethylglycyl,
glutaminyl,
glutamyl,
methionyl,
N-methylalanyl,
N-methylprolyl,
prolyl,
pyro-glutamyl,
sarcosyl,
seryl,
threonyl,
$H_3C-C(O)-HN-(CH_2)_q-C(O)-$, wherein q is an integer from 1 to 8, and
$H_3C-C(O)-HN-CH_2CH_2-O-(CH_2CH_2O)_r-CH_2-C(O)-$, wherein r is an integer from 1 to 8.

5. A compound according to claim 4, wherein $Xaa_2$ is sarcosyl.

6. The compound according to claim 1 wherein $Xaa_3$ is selected from the group consisting of
alanyl,
asparaginyl,
aspartyl,
glutaminyl,
glutamyl,
glycyl,
leucyl,
methionyl,
phenylalanyl,
prolyl, and
seryl.

7. A compound according to claim 6 wherein $Xaa_3$ is glycyl.

8. A compound according to claim 1 wherein $Xaa_4$ is selected from the group consisting of
alloisoleucyl,
allylglycyl,
2-aminobutyryl,
(1R,4S)-1-aminocyclopent-2-ene-4-carbonyl,
aspartyl,
3-(5-bromothien-2-yl)alanyl,
3-(3-chlorophenyl)alanyl,
3-(4-chlorophenyl)alanyl,
3-(3-cyanophenyl)alanyl,
cysteinyl(S-ethyl),
cysteinyl(S-methyl),
2,4-aminobutanoyl,
2,3-diaminopropionyl,
3-(3,4-dimethoxyphenyl)alanyl,
3-(3-fluorophenyl)alanyl,
3-(4-fluorophenyl)alanyl,
histidyl,
homophenylalanyl,
homoseryl,
lysyl(N-epsilon-acetyl),
methionyl(sulfone),
methionyl(sulfoxide),
3-(4-methylphenyl)alanyl,
3-(naphth-1-yl)alanyl,
3-(naphth-2-yl)alanyl,
ornithyl,
phenylglycyl,
prolyl,
3-(3-pyridyl)alanyl,
seryl(O-benzyl),
styrylalanyl,
1,2,3,4-tetrahydroisoquinoline-3-carbonyl,
3-(thiazoyl)alanyl,
3-(thien-2-yl)alanyl,
D-3-(thien-2-yl)alanyl,
tryptyl,
tyrosyl, and
D-valyl.

9. A compound according to claim 8 wherein $Xaa_4$ is selected from the group consisting of
alloisoleucyl,
allylglycyl,
2-aminobutyryl,
(1R,4S)-1-aminocyclopent-2-ene-4-carbonyl,
3-(5-bromothienyl-2-yl)alanyl,
3-(3-chlorophenyl)alanyl,
3-(4-chlorophenyl)alanyl,
3-(3-cyanophenyl)alanyl,
cysteinyl(S-ethyl),
cysteinyl(S-methyl),
2,4-diaminobutanoyl,
2,3-diaminopropionyl,
3-(3,4-dimethoxyphenyl)alanyl,
3-(3-fluorophenyl)alanyl,
3-(4-fluorophenyl)alanyl,
histidyl,
homophenylalanyl,
homoseryl,
lysyl(N-epsilon-acetyl),
methionyl(sulfone),
methionyl(sulfoxide),
3-(4-methylphenyl)alanyl, 3-(naphth-1-yl)alanyl,
3-(naphth-2-yl)alanyl,
ornithyl,
phenylglycyl,
prolyl,
3-(3-pyridyl)alanyl,
seryl(O-benzyl),
styrylalanyl,
1,2,3,4-tetrahydroisoquinoline-3-carbonyl,
3-(thiazolyl)alanyl,
3-(thien-2-yl)alanyl,
D-3-(thien-2-yl)alanyl,
tryptyl,
tyrosyl, and
D-valyl.

10. A compound according to claim 1, wherein $Xaa_5$ is selected from the group consisting of
D-alanyl,
alloisoleucyl,
D-alloisoleucyl,
D-allothreonyl,
D-allylglycyl,
D-2-aminobutyryl,
D-3-(4-aminophenyl)alanyl,
D-asparaginyl,
D-aspartyl,
D-3-(4,4'-biphenyl)alanyl,
D-t-butylglycyl,
D-3-(4-chlorophenyl)alanyl,
D-citrullyl,
D-3-(3-cyanophenyl)alanyl,
D-cyclohexylalanyl,
D-cyclohexylglycyl,
D-cysteinyl,
D-cysteinyl(S-t-butyl),
dehydroleucyl,
D-3-(3,4-difluorophenyl)alanyl,
D-3-(3,4-dimethoxyphenyl)alanyl,
D-glutaminyl,
D-glutamyl,
glycyl,
D-histidyl,
D-homoisoleucyl,
D-homophenylalanyl,
D-homoseryl,
isoleucyl,
D-isoleucyl,
D-leucyl,
D-lysyl,
D-lysyl(N-epsilon-nicotinyl),
D-methionyl,
D-3-(4-methylphenyl)alanyl,
D-3-(naphth-1-yl)alanyl,
D-3-(naphth-2-yl)alanyl,
D-neopentylglycyl,
D-3-(4-nitrophenyl)alanyl,
D-norleucyl,
D-norvalyl,
D-ornithyl,
D-penicillaminyl,
D-penicillaminyl(S-acetamidomethyl),
D-penicillaminyl(S-benzyl),
D-penicillaminyl(S-methyl),
D-phenylalanyl,
prolyl,
D-prolyl,
D-3-(3-pyridyl)alanyl,
D-seryl,
D-seryl(O-benzyl),
D-3-(thien-2-yl)alanyl,
D-threonyl,
D-threonyl(O-benzyl),
D-3-(3-trifluoromethylphenyl)alanyl,
D-3-(3,4,5-trifluorophenyl)alanyl,
D-tryptyl,
D-tyrosyl(O-benzyl),
D-tyrosyl(O-ethyl),
D-tyrosyl, and
D-valyl.

11. A compound according to claim 10 wherein $Xaa_5$ is selected from the group consisting of
isoleucyl,
D-isoleucyl, and
D-leucyl.

12. A compound according to claim 1 wherein $Xaa_6$ is selected from the group consisting of
alanyl,
allothreonyl,
D-allothreonyl,
allylglycyl,
asparaginyl,
cysteinyl,
glutaminyl,
glycyl,
histidyl,
homoseryl,
D-homoseryl,
3-(4-hydroxymethylphenyl)alanyl,
isoleucyl,
lysyl(N-epsilon-acetyl),
methionyl,
3-naphth-1-yl)alanyl,
3-naphth-2-yl)alanyl,
norvalyl,
octylglycyl,
ornithyl,
penicillaminyl,
prolyl,
3-(3-pyridyl)alanyl,
seryl,
D-seryl,
threonyl,
tryptyl, and
tyrosyl.

13. A compound according to claim 12 wherein $Xaa_6$ is selected from the group consisting of
seryl, and
threonyl.

14. A compound according to claim 1 wherein $Xaa_7$ is selected from the group consisting of
alanyl,
allylglycyl,
2-aminobutyryl,
arginyl,
asparaginyl,
aspartyl,
3-(4-carboxyamidophenyl)alanyl,
citrullyl,
cyclohexylalanyl,
cysteinyl,
glutaminyl,
D-glutaminyl,
glutamyl,
glycyl,
histidyl,
homoalanyl,
homoleucyl,
homoseryl,
D-homoseryl,
isoleucyl,
leucyl,
D-leucyl,
lysyl(N-epsilon-acetyl),
lysyl(N-epsilon-isopropyl),
methionyl(sulfone),
methionyl(sulfoxide),
methionyl,
3-(naphth-1-yl)alanyl,
D-3-(naphth-1-yl)alanyl,
3-(naphth-2-yl)alanyl,
D-3-(naphth-2-yl)alanyl,
norleucyl,
norvalyl,
D-norvalyl,
octylglycyl,
penicillaminyl,
phenylalanyl,
propargylglycyl,
3-(3-pyridyl)alanyl,
seryl,
D-seryl,
threonyl,
tryptyl,
tyrosyl, and
valyl.

15. A compound according to claim 14 wherein $Xaa_7$ is selected from the group consisting of
glutaminyl,
norvalyl, and
seryl.

16. A compound according to claim 1 wherein $Xaa_8$ is selected from the group consisting of
alanyl,
alloisoleucyl,
D-alloisoleucyl,
allylglycyl,
aspartyl,
t-butylglycyl,
citrullyl,
cyclohexylglycyl,
cysteinyl,
glutamyl,
glycyl,
homoseryl,
isoleucyl,
D-isoleucyl,
leucyl,
lysyl(N-epsilon-acetyl),
methionyl,
3-(naphth-1-yl)alanyl,
3-(naphth-2-yl)alanyl,
norvalyl,
penicillaminyl,
phenylalanyl,
prolyl,
seryl,
tryptyl,
tyrosyl, and
valyl.

17. A compound according to claim 16 wherein $Xaa_8$ is isoleucyl.

18. A compound according to claim 1 wherein $Xaa_9$ is selected from the group consisting of
[(4-amino(N-isopropyl)methyl)phenyl]alanyl,
3-(4-amino(N-isopropylphenyl)alanyl,
arginyl,
arginyl($N^G N^{G'}$diethyl),
citrullyl,
3-(cyclohexyl)alanyl(4-N-isopropyl),
glycyl[4-piperidinyl(N-amidino)],
(3-guanidino)alanyl,
3-(4-guanidinophenyl)alanyl,
histidyl,
homoarginyl,
lysyl,
lysyl(N-epsilon-isopropyl),
lysyl(N-epsilon-nicotinyl),
norarginyl,
ornithyl(N-delta-isopropyl),
ornithyl(N-delta-nicotinyl),
ornithyl[N-delta-(2-imidazolinyl)],
[4-piperidinyl(N-amidino)]alanyl, and
[3-pyrrolidinyl(2-N-amidino)]alanyl.

19. A compound according to claim 18 wherein $Xaa_9$ is arginyl.

20. A compound according to claim 1 wherein $Xaa_{10}$ is selected from the group consisting of
D-alanyl,
2-aminobutyryl,
2-aminoisobutyryl, t-butylglycyl,
homoprolyl,
hydroxyprolyl,
isoleucyl,
leucyl,
phenylalanyl,
prolyl,
D-prolyl,
seryl,
1,2,3,4-tetrahydroisoquinoline-3-carbonyl,
threonyl, and
valyl.

21. A compound according to claim 20 wherein $Xaa_{10}$ is prolyl.

22. A compound according to claim 1 wherein $Xaa_{11}$ is selected from the group consisting of
D-alanylamide,
D-alanylethylamide,
azaglycylamide,
NH-cyclobutyl,
NH-cycloheptyl,
NH-1-(cyclohexyl)ethyl,
NH-2-(cyclohexyl)ethyl,
NH-2-(ethoxy)ethyl,
NH-ethyl,
glycylamide,
glycylethylamide,
NH-hexyl,
NH-2-(hydroxy)ethyl,
NH-isoamyl,
NH-isobutyl,
NH-2-(isopropoxy)ethyl,
NH-isopropyl,
NH-2-(methoxy)ethyl,
NH-3-(methoxy)propyl,
NH-propyl,
NH-2-(1-pyrrolidine)ethyl,
sarcosylamide,
serylamide, and
D-serylamide.

23. A compound according to claim 22 wherein $Xaa_{11}$ is selected from the group consisting of
D-alanylamide, and
NH-ethyl.

24. A compound according to claim 1 wherein
$Xaa_1$ is selected from the group consisting of
  acetyl, and
  6-methylnicotinyl;
$Xaa_2$ is sarcosyl;
$Xaa_3$ is glycyl;
$Xaa_4$ is selected from the group consisting of
  alloisoleucyl,
  allylglycyl,
  2-aminobutyryl,
  (1R,4S)-1-aminocyclopent-2-ene-4-carbonyl,
  3-(5-bromothion-2-yl)alanyl,
  3-(3-chlorophenyl)alanyl,
  3-(4-chlorophenyl)alanyl,
  3-(3-cyanophenyl)alanyl,
  cysteinyl(S-ethyl),
  cysteinyl(S-methyl),
  2,3-diaminopropionyl,
  2,4-diaminobutanoyl,
  3-(3,4-dimethoxyphenyl)alanyl,
  3-(3-fluorophenyl)alanyl,
  3-(4-fluorophenyl)alanyl,
  histidyl,
  homophenylalanyl,
  homoseryl,
  lysyl(N-epsilon-acetyl),
  methionyl(sulfone),
  methionyl(sulfoxide),
  3-(4-methylphenyl)alanyl,
  3-(naphth-1-yl)alanyl,
  3-(naphth-2-yl)alanyl,
  ornithyl,
  phenylglycyl,
  prolyl,
  3-(3-pyridyl)alanyl,
  seryl(O-benzyl),
  styrylalanyl,
  1,2,3,4-tetrahydroisoquinoline-3-carbonyl,
  3-(thiazolyl)alanyl,
  3-(thien-2-yl)alanyl,
  D-3-(thien-2-yl)alanyl,
  tryptyl,
  tyrosyl, and
  D-valyl,
$Xaa_5$ is selected from the group consisting of
  isoleucyl,
  D-isoleucyl, and
  D-leucyl;
$Xaa_6$ is selected from the group consisting of
  seryl, and
  threonyl;
$Xaa_7$ is selected from the group consisting of
  glutaminyl,
  norvalyl, and
  seryl;
$Xaa_8$ is isoleucyl;
$Xaa_9$ is arginyl;
$Xaa_{10}$ is prolyl; and
$Xaa_{11}$ is selected from the group consisting of
  D-alanylamide, and
  NH-ethyl.

25. A composition comprising a compound of claim 1 and a pharmaceutically acceptable carrier.

26. A compound, or a pharmaceutically acceptable salt thereof, selected from the group consisting of
N-Ac-Sar-Gly-5-BrThiAla-D-Leu-Thr-Nva-Ile-Arg-ProNH-ethyl,
N-Ac-Sar-Gly-2-Nal-D-Leu-Thr-Nva-Ile-Arg-ProNH-ethyl,
N-Ac-Sar-Gly-Orn-D-Leu-Thr-Nva-Ile-Arg-ProNH-ethyl,
N-Ac-Sar-Gly-4-ClPheAla-D-Leu-Thr-Nva-Ile-Arg-ProNH-ethyl,
N-Ac-Sar-Gly-HPheAla-D-Leu-Thr-Nva-Ile-Arg-ProNH-ethyl,
N-Ac-Sar-Gly-Cys(Me)-D-Leu-Thr-Nva-Ile-Arg-ProNH-ethyl,
N-Ac-Sar-Gly-Cys(Et)-D-Leu-Thr-Nva-Ile-Arg-ProNH-ethyl, and N-Ac-Sar-Gly-Tyr-D-Leu-Thr-Nva-Ile-Arg-ProNH-ethyl.

27. A compound, or salt thereof, selected from the group consisting of

N-Ac-Sar-Gly-Lys(Ac)-D-Leu-Thr-Nva-Ile-Arg-ProNH-ethyl,
N-Ac-Sar-Gly-Pro-D-Leu-Thr-Nva-Ile-Arg-ProNH-ethyl,
N-Ac-Sar-Gly-3-CNPheAla-D-Leu-Thr-Nva-Ile-Arg-ProNH-ethyl,
N-Ac-Sar-Gly-Cys(Et)-D-Leu-Thr-Nva-Ile-Arg-ProNH-ethyl,
N-Ac-Sar-Gly-4-ThzAla-D-Leu-Thr-Nva-Ile-Arg-ProNH-ethyl,
N-Ac-Sar-Gly-(1R,4S)-AmCyeCO-D-Leu-Thr-Nva-Ile-Arg-ProNH-ethyl,
N-Ac-Sar-Gly-diOMePheAla-D-Leu-Thr-Nva-Ile-Arg-ProNH-ethyl,
N-Ac-Sar-Gly-MePheAla-D-Leu-Thr-Nva-Ile-Arg-ProNH-ethyl,
N-Ac-Sar-Gly-3-ClPheAla-D-Leu-Thr-Nva-Ile-Arg-ProNH-ethyl,
N-Ac-Sar-Gly-2-ThiAla-D-Leu-Thr-Nva-Ile-Arg-ProNH-ethyl,
N-Ac-Sar-Gly-PheGly-D-Leu-Thr-Nva-Ile-Arg-ProNH-ethyl,
N-Ac-Sar-Gly-2,4-Diabu-D-Leu-Thr-Nva-Ile-Arg-ProNH-ethyl,
N-Ac-Sar-Gly-Met($O_2$)-D-Leu-Thr-Nva-Ile-Arg-ProNH-ethyl,
N-Ac-Sar-Gly-1-Nal-D-Leu-Thr-Nva-Ile-Arg-ProNH-ethyl,
N-Ac-Sar-Gly-2-Abu-D-Leu-Thr-Nva-Ile-Arg-ProNH-ethyl,
N-Ac-Sar-Gly-Met(O)-D-Leu-Thr-Nva-Ile-Arg-ProNH-ethyl,
N-Ac-Sar-Gly-His-D-Leu-Thr-Nva-Ile-Arg-ProNH-ethyl,
N-Ac-Sar-Gly-Trp-D-Leu-Thr-Nva-Ile-Arg-ProNH-ethyl,
N-Ac-Sar-Gly-Tic-D-Leu-Thr-Nva-Ile-Arg-ProNH-ethyl,
N-Ac-Sar-Gly-StyAla-D-Leu-Thr-Nva-Ile-Arg-ProNH-ethyl,
N-Ac-Sar-Gly-AllylGly-D-Leu-Thr-Nva-Ile-Arg-ProNH-ethyl,
N-Ac-Sar-Gly-4-FPheAla-D-Leu-Thr-Nva-Ile-Arg-ProNH-ethyl,
N-Ac-Sar-Gly-2,3-Diapr-D-Leu-Thr-Nva-Ile-Arg-ProNH-ethyl,
N-Ac-Sar-Gly-Met($O_2$)-D-Leu-Thr-Nva-Ile-Arg-ProNH-ethyl,
N-Ac-Sar-Gly-3-PyrAla-D-Leu-Thr-Nva-Ile-Arg-ProNH-ethyl,
N-Ac-Sar-Gly-4-ClPheAla-D-Leu-Thr-Nva-Ile-Arg-ProNH-ethyl,
N-Ac-Sar-Gly-1-Nal-D-Leu-Thr-Nva-Ile-Arg-ProNH-ethyl,
N-Ac-Sar-Gly-2-Nal-D-Leu-Thr-Nva-Ile-Arg-ProNH-ethyl,
N-Ac-Sar-Gly-3-FPheAla-D-Leu-Thr-Nva-Ile-Arg-ProNH-ethyl,
N-Ac-Sar-Gly-HPheAla-D-Leu-Thr-Nva-Ile-Arg-ProNH-ethyl,
N-Ac-Sar-Gly-4-FPheAla-D-Leu-Thr-Nva-Ile-Arg-ProNH-ethyl,
N-Ac-Sar-Gly-alloIle-D-Leu-Thr-Nva-Ile-Arg-ProNH-ethyl,
N-Ac-Sar-Gly-Ser(Bzl)-D-Leu-Thr-Nva-Ile-Arg-ProNH-ethyl,
N-Ac-Sar-Gly-HSer-D-Leu-Thr-Nva-Ile-Arg-ProNH-ethyl,
N-Ac-Sar-Gly-(1R,4S)-AmCyeCO-D-Leu-Thr-Nva-Ile-Arg-ProNH-ethyl,
N-6MeNic-Sar-Gly-(1R,4S)-AmCyeCO-D-Leu-Thr-Nva-Ile-Arg-ProNH-ethyl,
N-Ac-Sar-Gly-2-ThiAla-D-Leu-Thr-Nva-Ile-Arg-ProNH-ethyl,
N-Ac-Sar-Gly-3-CNPhe-D-Leu-Thr-Nva-Ile-Arg-Pro-D-AlaNH$_2$,
N-Ac-Sar-Gly-D-Val-D-Ile-Thr-Nva-Ile-Arg-ProNH-ethyl,
N-Ac-Sar-Gly-D-2-ThiAla-D-Leu-Thr-Nva-Ile-Arg-Pro-D-AlaNH$_2$,
N-Ac-Sar-Gly-(1R,4S)-AmCyeCO-D-Leu-Thr-Gln-Ile-Arg-ProNH-ethyl, and
N-Ac-Sar-Gly-D-Val-Ile-Thr-Nva-Ile-Arg-ProNH-ethyl.

28. A composition comprising a pharmaceutically acceptable carrier and a compound of claim 1 in an amount effective to inhibit angiogenesis.

29. A composition comprising a pharmaceutically acceptable carrier and a compound of claim 1 in an amount effective to inhibit growth of tumor cells.

* * * * *

UNITED STATES PATENT AND TRADEMARK OFFICE
CERTIFICATE OF CORRECTION

PATENT NO. : 6,753,408 B1
APPLICATION NO. : 09/718591
DATED : June 22, 2004
INVENTOR(S) : Fortuna Haviv et al.

It is certified that error appears in the above-identified patent and that said Letters Patent is hereby corrected as shown below:

Col. 38, line 59
After the word "methionyl" insert
--     N-methylalanyl,
N-methylprolyl,
prolyl,
pyro-glutamyl,
sarcosyl,
seryl,
threonyl,
$H_3C-C(O)-HN-(CH_2)_q-C(O)-$, wherein q is an integer from 1 to 8, and
$H_3C-C(O)-HN-CH_2CH_2-O-(CH_2CH_2O)_r-CH_2-C(O)-$, wherein r is an integer from 1 to 8;
with the proviso that $Xaa_1$ is absent when $Xaa_2$ is N-methylprolyl, $H_3C-C(O)-HN-(CH_2)_q-C(O)-$, or $H_3C-C(O)-HN-CH_2CH_2-O-(CH_2CH_2O)_r-CH_2-C(O)-$;

$Xaa_3$ is an amino acyl residue selected from the group consisting of alanyl, -- before the word "asparaginyl,".

Col. 39, line 12
After "3-(4-chlorophenyl)alanyl," insert -- 3-(3-cyanophenyl)alanyl,
cysteinyl(S-ethyl),
cysteinyl(S-rnethyl),
2,4-diaminobutanoyl,
2,3-diaminopropionyl,
3-(3,4-dimethoxyphenyl)alanyl,
3-(3-fluorophenyl)alanyl,
3-(4-fluorophenyl)alanyl,
histidyl,
homophenylalanyl,
homoseryl,
lysyl(N-epsilon-acetyl),
methionyl(sulfone),
methionyl(sulfoxide),
3-(4-methylphenyl)alanyl,
3-(naphth-1-yl)alanyl,
3-(naphth-2-yl)alanyl, --
before the word "ornithyl,".

UNITED STATES PATENT AND TRADEMARK OFFICE
CERTIFICATE OF CORRECTION

PATENT NO. : 6,753,408 B1
APPLICATION NO. : 09/718591
DATED : June 22, 2004
INVENTOR(S) : Fortuna Haviv et al.

It is certified that error appears in the above-identified patent and that said Letters Patent is hereby corrected as shown below:

Col. 39, line 30
After the word "D-alloisoleucyl," insert the word --D-allothrenoyl,-- before the word "D-allylglycyl,".

Col. 40, line 37
After the word "methionyl," insert --3-(naphth-l-yl)alanyl,-- before "3-(naphth-2yl)alanyl,".

Col. 41, line 8
After the word "D-leucyl," insert --lysyl(N-epsilon-acetyl), lysyl(N-epsilon-isopropyl), methionyl(sulfone), methionyl(sulfoxide), methionyl, 3-(naphth-1-yl)alanyl, D-3-(naphth-1-yl)alanyl, 3-(naphth-2-yl)alanyl, D-3-(naphth-2-yl)alanyl, norleucyl, norvalyl, D-norvalyl, octylglycyl, penicillaminyl, phenylalanyl, propargylglycyl,-- before "3-(3-pyridyl)alanyl,".

Col. 44, line 7
Replace "2,4-aminobutanoyl,".
with --2,4-diaminobutanoyl,--.

Col. 44, line 47
Replace "3-(5-bromothienyl-2-yl)alanyl,".
with --3-(5-bromothien-2-yl)alanyl,--.

Col. 46, line 65
After the word "threonyl," insert the word --D-threonyl,-- before "tryptyl, and".

Col. 48, line 8
Replace "cyclolhexylglycyl,".
with --cyclohexylglycyl,--.

Col.51, line 1
Replace "Leu".
with --Ile--

UNITED STATES PATENT AND TRADEMARK OFFICE
CERTIFICATE OF CORRECTION

PATENT NO. : 6,753,408 B1
APPLICATION NO. : 09/718591
DATED : June 22, 2004
INVENTOR(S) : Fortuna Haviv et al.

It is certified that error appears in the above-identified patent and that said Letters Patent is hereby corrected as shown below:

Col. 51, line 20
Replace "Gly-MePheAla".
with --Gly-4-MePheAla- --.

Col. 52, line 3
Replace "Leu".
with --Ile--.

Col. 52, line 5
Replace "Leu".
with --Ile--.

Col. 52, line 7
Replace "Leu".
with --Ile--.

Col. 52, line 10
Replace "Leu".
with --Ile--.

Col. 52, line 12
Replace "Leu".
with --Ile--.

Col. 52, line 14
Replace "Leu".
with --Ile--.

Col, 52, line 16
Replace "Leu'.
with --Ile--.

Col. 52, line 18
Replace "Leu".
with --Ile--.

Col.. 52, line 20
Replace "Leu".
with --Ile--.

UNITED STATES PATENT AND TRADEMARK OFFICE
CERTIFICATE OF CORRECTION

PATENT NO. : 6,753,408 B1
APPLICATION NO. : 09/718591
DATED : June 22, 2004
INVENTOR(S) : Fortuna Haviv et al.

It is certified that error appears in the above-identified patent and that said Letters Patent is hereby corrected as shown below:

Col. 52, line 26
Replace "Leu".
with --Ile--.

Signed and Sealed this

Ninth Day of January, 2007

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 11
<212> TYPE: PRT
<213> ORGANISM: Antiangiogenic Peptide
<220> FEATURE:
<221> NAME/KEY: VARIANT
<222> LOCATION: (1)...(1)
<223> OTHER INFORMATION: Xaa = R1-(CH2)n-C(O)- wherein R is
      N-acetylamino at position 1
<221> NAME/KEY: VARIANT
<222> LOCATION: (2)...(2)
<223> OTHER INFORMATION: Xaa = Ala, B-Ala , Asn, Cit, Gly(Et), Gln, Glu,
      Met, N-MeAla, N-MePro, Pro, Glu(pyro), and Sar at
      position 2
<221> NAME/KEY: VARIANT
<222> LOCATION: (2)...(2)
<223> OTHER INFORMATION: Xaa =  Ser, Thr, H3C-C(O)-HN-(CH2)q-C(O)-,
      wherein q is an integer, and
      H3C-C(O)-HN-CH2CH2-O-(CH2CH2O)r-CH2-C(O)-, wherein r is an integer
      at position 2
<221> NAME/KEY: VARIANT
<222> LOCATION: (3)...(3)
<223> OTHER INFORMATION: Xaa = Ala, Asn, Asp, Gln, Glu, Gly, Leu, Met,
      PheAla, Pro, and Ser at position 3
<221> NAME/KEY: VARIANT
<222> LOCATION: (4)...(4)
<223> OTHER INFORMATION: Xaa = AlloIle, AllylGly, 2-Abu, (IR,4S)AmCyeCO,
      Asp, 5-BrThiAla, 3-ClPheAla, 4-ClPheAla, 3-CNPheAla, Cys(Et),
```

-continued

```
        Cys(Me), 2,3-Diapr, 2,4-Diabu, 3,4-diOMePheAla at position 4
<221> NAME/KEY: VARIANT
<222> LOCATION: (4)...(4)
<223> OTHER INFORMATION: Xaa = 3-FPheAla, 4-FPheAla, His, HPheAla, HSer,
      Lys(Ac), Met(O2), Met(O), 4-MePheAla, 1-Nal, 2-Nal, Orn, PheGly,
      Pro, 3-Pal, 3-ThzAla, 2-ThiAla at position 4
<221> NAME/KEY: VARIANT
<222> LOCATION: (4)...(4)
<223> OTHER INFORMATION: Xaa = Ser(Bzl), StyAla, Tic, Trp, and Tyr at
      position 4
<221> NAME/KEY: VARIANT
<222> LOCATION: (5)...(5)
<223> OTHER INFORMATION: Xaa = AlloIle, deLeu, Gly, Ile, and Pro at
      position 5
<221> NAME/KEY: VARIANT
<222> LOCATION: (6)...(6)
<223> OTHER INFORMATION: Xaa = Ala, AlloThr, AllylGly, Asn, Cys, Gln,
      Gly, His, HSer, 4-OHMePheAla, Ile, Lys(Ac), Met, 1-Nal, 2-Nal,
      Nva, OctylGly, Orn, Pen, Pro, 3-Pal, Ser, Thr, Trp, and Tyr at
      position 6
<221> NAME/KEY: VARIANT
<222> LOCATION: (7)...(7)
<223> OTHER INFORMATION: Xaa = Ala, AllylGly, 2-Abu, Arg, Asn, Asp,
      CamdPheAla, Cit, Cha, Cys, Gln, Glu, Gly, His, HAla, HIle, HSer,
      Ile, Leu, Lys(Ac) at position 7
<221> NAME/KEY: VARIANT
<222> LOCATION: (7)...(7)
<223> OTHER INFORMATION: Xaa = Lys(Isp), Met(O2), Met(O), Met, 1-Nal,
      2-Nal, Nle, Nva, OctylGly, Pen, PheAla, PropGly, 3-Pal, Ser, Thr,
      Trp, Tyr, and Val at position 7
<221> NAME/KEY: VARIANT
<222> LOCATION: (8)...(8)
<223> OTHER INFORMATION: Xaa = Ala, AlloIle, AllylGly, Asp, Gly(t-Bu),
      Cit, Cha, Cys, Glu, Gly, HSer, Ile, Leu, Lys(Ac), Met,1-Nal,
      2-Nal, Nva, Pen, PheAla, Pro, Ser, Trp, Tyr, and Val at position 8
<221> NAME/KEY: VARIANT
<222> LOCATION: (9)...(9)
<223> OTHER INFORMATION: Xaa = AimPheAla, AiPheAla, Arg, Arg(diethyl),
      Cit, Cha(Isp), Gly(pipad), GuaAla, 4-GuaPheAla, His, HArg, Lys,
      Lys(Isp)  at position 9
<221> NAME/KEY: VARIANT
<222> LOCATION: (9)...(9)
<223> OTHER INFORMATION: Xaa = Lys(Nic), NArg, Orn(Isp), Orn(Nic),
      Orn(Imd), (pipamid)Ala, and (pyramid)Ala at position 9
<221> NAME/KEY: VARIANT
<222> LOCATION: (10)...(10)
<223> OTHER INFORMATION: Xaa = 2-Abu, Aib, Gly(t-Bu), HPro, OHPro, Ile,
      Leu, PheAla, Pro, Ser, Tic, Thr, and Val at position 10
<221> NAME/KEY: VARIANT
<222> LOCATION: (11)...(11)
<223> OTHER INFORMATION: Xaa = AzaGlyNH2, GlyNH2, GlyNH-ethyl, SarNH2,
      and SerNH2 at position 11

<400> SEQUENCE: 1

Xaa Xaa Xaa Xaa Xaa Xaa Xaa Xaa Xaa Xaa Xaa
 1               5                   10
```